US007094767B2

(12) United States Patent
Armstrong et al.

(10) Patent No.: US 7,094,767 B2
(45) Date of Patent: Aug. 22, 2006

(54) POLYNUCLEOTIDE HERPES VIRUS VACCINE

(75) Inventors: Marcy E. Armstrong, Schwenksville, PA (US); Robert D. Keys, Norristown, PA (US); John A. Lewis, Norristown, PA (US); Margaret A. Liu, Rosemont, PA (US); William L. McClements, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 464 days.

(21) Appl. No.: 09/835,699

(22) Filed: Apr. 16, 2001

(65) Prior Publication Data

US 2002/0147167 A1 Oct. 10, 2002

Related U.S. Application Data

(63) Continuation of application No. 08/720,758, filed on Oct. 1, 1996, now abandoned, which is a continuation-in-part of application No. 08/715,309, filed on Sep. 18, 1996, now abandoned, which is a continuation of application No. 08/279,459, filed on Jul. 22, 1994, now abandoned.

(51) Int. Cl.
*A61K 48/00* (2006.01)

(52) U.S. Cl. .................................... 514/44; 435/320.1
(58) Field of Classification Search ................ 514/44; 435/320.1; 536/23.1, 23.2, 23.72
See application file for complete search history.

(56) References Cited

U.S. PATENT DOCUMENTS

| 4,374,127 A | 2/1983 | Larson et al. ............. 424/231.1 |
| 5,244,792 A | 9/1993 | Burke et al. ................ 435/69.3 |

FOREIGN PATENT DOCUMENTS

| EP | 0 406 857 A1 | 1/1991 |
| WO | WO 88/00971 | 2/1988 |
| WO | WO 90/11092 | 10/1990 |
| WO | WO 9603510 A1 | 2/1996 |

OTHER PUBLICATIONS

Cox et al, J. Virol. 67(9): 5664 (1993).*
Gallichan, W. et al. "Mucosal Immunity and Protection after Intranasal Immunization with Recombinant Adenovirus Expressing Herpes Simplex Virus Glycoprotein B". The Journal of Infe. Disease 1993, vol. 168, pp. 622–629.
Byars et al. "Vaccinating guinea pigs with recombinant glycoprotein D of herpes simplex virus in an efficaious adjuvant formulation elicits protection against vaginal infection"; Vaccine 1994, vol. 12, No. 3, pp. 200–209.
Straus et al. "Induction and Enhancement of Immune Responses to Herpes Simplex Virus Type 2 in Humans by Use of a Recombinant Glycoprotein D Vaccine", J. of Infectious Diseases, vol. 167, pp. 1045–1052 (1993).

Ghiasi et al. "Expression of Seven Herpes Simplex Virus Type 1 Glycoproteins (gB, gC, gD, gE, gG, gH and gI): Comparative Protection against Lethal Challange in Mice"; J. Virology, Apr. 1994, pp. 2118–2126.
Wachsman et al. "Protection from herpes simplex virus type 2 is associated with T cells involved in delayed type hypersensitivity that recognize glycosylation–related epitopes in glycopretein D", Vaccine, vol. 10, No. 7, pp. 447–454. (1992).
Ghiasi et al. "Immunoselection of recombinant baculoviruses expressing high levels of biologically active herpes simplex virus type 1 glycoprotein D", Arch. Virol (1991) 121: 163–178.
Burke, "Current developments in herpes simplex virus vaccines", Virology, vol. 4, 1993, pp. 187–197.
Burke, "Development of a Herpes Simplex Virus Subunit Glycoprotein Vaccine for Prophylactic and Therapeutic Use", Reviews of Infectious Diseases, vol. 13, Suppl 11, p S906–S911 (1991).
Lasky, "From Virus to Vaccine: Recombinant Mammalian Cell Lines as Substrares for the Production of Herpes Simplex Virus Vaccines", J. of Med. Virology, 31:pp. 59–61 (1990).
Aurelian et al. "Immune Responses to Herpes Simplex Virus in Guinea Pigs (Footpad Model) and Mice Immunized with Vaccinia Virus Recombinants Containing Herpes Simplex Virus Glycoprotein D", Review of Infec. Diseases, vol. 13, (Suppl 11) S924–934 (1991).
Rooney et al. "Live Vaccinia Virus Recombinants Expressing Herpes Simplex Virus Genes", Reveiws of Infec. Diseases, vol. 13 (Suppl 11) p S898–903 (1991).
Ritchie et al. "Passive Transfer of Anti–Herpes Simplex Virus Type 2 Monoclonal and Polyclonal Antibodies Protect Against Herpes Simplex Virus Type 1–induced but not Herpes Simplex Virus Type 2–induced Stromal Keratitis", Invest. Ophthal & Vis. Science, vol. 34, No. 8, pp. 2460–2468 (1993).
Montgomery et al. "Heterologous and Homologous Protection Against Influenza A by DNA vaccination: Optimization of DNA Vectors", DNA and Cell Biology, vol. 12, No. 9, pp. 777–783 (1993).

(Continued)

Primary Examiner—James Martinell

(57) ABSTRACT

Genes encoding herpes simplex virus type 2 (HSV-2) proteins were cloned into eukaryotic expression vectors to express the encoded proteins in mammalian muscle cells in vivo. Animals were immunized by injection of these DNA constructs, termed polynucleotide vaccines or PNV, into their muscles. In a DNA titration, it was found that a single immunization of ≧0.5 µg of (one) PNV, gave >90% seroconversion by ten weeks post immunization. Immune antisera neutralized both HSV-2 and HSV-1 in cell culture. When animals were challenged with HSV-2, significant (p<0.001) protection from lethal infection was achieved following PNV vaccination. DNA constructs may be full-length, truncated and/or mutated forms and may be delivered along or in combination in order to optimize immunization and protection from HSV infection.

16 Claims, 17 Drawing Sheets

OTHER PUBLICATIONS

Ulmer et al. "Heterologous Protection Against Influenza by Injection of DNA Encoding a Viral Protein", Science, vol. 259, pp. 1745–1749 (1993).

Browne et al. "Analysis of protective immune responses to the glycoprotein H–glycoprotein L complex of herpes simplex virus type 1", J. of Gen. Virology, Vo. 74, pp. 2813–2817 (1993).

Stanberry et al. "Vaccination with Recombinant Herpes Simplex Virus Glycoproteins: Protection Against Initial and Recurrent Genital Herpes", Jour. of Infec. Dis., vol. 155, No. 5, pp. 914–920 (1987).

Eisenberg et al. "Synthetic Glycoprotein D–related Peptides Protect Mice against Herpes Simplex Virus Challange", J. of Virology, vol. 56, No. 3, pp. 1014–1017 (1985).

Long et al. "Glycoprotein D Protects Mice Against Lethal Challange with Herpes Simplex Virus Types 1 and 2", Infec. and Immunity, vol. 37, No. 2, pp. 761–764 (1984).

Dix et al. "Use of Monolonal Antibody Directed Against Herpes Simplex Virus Glycoprotein to Protect Mice Against Acute Virus–Induced Neurological Disease", Infection and Immunity, vol. 34, No. 1, pp. 192–199 (1981).

Stanberry et al. "Herpes simplex virus glycoprotein immunotherapy of recurrent genital herpes: factors influencing efficacy", Antiviral Res. vol. 11, pp. 203–214 (1989).

Kino et al. "Immunogenicity of herpes simplex virus glycoprotein gB–1 related protein produced in yeast", Chemo-Sero–Ther. Res. Inst. Japan (1988).

McDermott et al. "Protection of Mice against Lethal Challange with Herpes Simplex Virus . . . Expressing HSV Glycoprotein B", Virology, vol. 169, pp. 244–247 (1989).

Schmid et al. "The Role of T cell Immunity in Control of Herpes Simplex Virus", Current Topics in Microbiology and Immunology, vol. 179, pp. 57–74 (1992).

Banks et al. "Recognition by and in Vitro Induction of Cytotoxic T Lymphocytes against Predicted Epitopes of the Immediate–Early Protein ICP27 of Herpes Simplex Virus", J. of Virology, vol. 67, No. 1, pp. 613–616 (1993).

Watanabe et al. "Induction of Antibodies to a KV Region by Gene Immunization", J. of Immuno. vol. 151, pp. 2871–2876 (1993).

Ellis et al. "New Vaccine Technologies", JAMA, vol. 271, No. 12, pp. 929–931.

Ho et al. "Liposome formulated interleukin–2 as an adjuvant of recombinant HSV glycoprotein gD for the treatment of recurrent genital HSV–2 in guinea pigs", Vaccine, vol. 10, Issue 4, pp. 209–213 (1992).

Friedman, "Progress Toward Human Gene Thereapy", Science, vol. 259, pp. 1275–1281 (1989).

Edgington, "Turning on Tumor Fighting T–Cells", Bio/Technology, vol. 11, Oct. 1993, pp. 1117–1119 (1993).

Manickan et al. "Protection against HSV infection by DNA vaccination: plasmid DNA encoding HSV–1 gB protects mice from HSV–1 zosteriform lesions", FASEB Jour. vol. 9, No. 3 p. A207 and Exper. Biol. 95, Part 1, Atlanta GA, USA (Apr. 9–13) (1995).

Ghiasi et al. "Vaccination of mice with herpes simplex virus type 1 glycoprotein–D DNA produces low levels of protection against lethal HSV–1 challange", Antiviral Res. vol. 28, No. 2, pp. 147–157 (1995).

Marwick, "Exciting Potential of DNA Vaccines Explored", JAMA, vol. 273, No. 18, pp. 1403–1404 (1995).

Liu et al. "Immune responses and pre–clinical efficacy of DNA vaccines for viral diseases", Int. Pharm. J., vol. 9, Suppl. 1, 10 (1995).

Shinya, "Recombinant DNA Integration with Herpes Simplex Gene . . . ", Patent Abstract of Japan, vol. 11, 332 (1987).

McClements et al. Prevention of LEthal HSV–2 Infection in Mice by Immunization with DNA encoding HSV–2 Glycoproteins, 20th Ann. Herpesvirus Workshop, Abs. #359, 1995.

McClements et al. "Immunization with DNA Vaccines Encoding GlcD or GlcB, alone or in combination, induces . . . ", Proc. Natl. Acad. Sci., vol. 93, pp. 11414–11420, (1996).

Lasky et al. "DNA Sequence Anlaysis of the Type–Common Glycoprotein–D Genes of Herpes Simplex Virus Types 1 and 2". DNA, vol. 3, No. 1, pp. 23–29.

* cited by examiner

□ 1.56 μg; ○ 0.78 μg V1J:gD DNA; ♦ saline

△ 200; 100; 25; 12.5; 6.25; 3.13 μg

| Group[a] | Survivors/ Total (%) | Mean Day to Death | Paralyzed/ Total (%) | Vaginal Virus Titer[b] | | |
|---|---|---|---|---|---|---|
| | | | | Day 2[c] | Day 4 | Day 6 |
| Vaccine, 10 μg | 8/10 (80) | 12.5 ± 0.7 | 5/10 (50) | 3.8 ± 1.9 | 2.3 ± 1.2 | <1.5 ± 0.0 |
| Vaccine, 100 μg | 10/10 (100)† | >21 | 0/10 (0)* | 3.0 ± 1.3∅ | 2.0 ± 0.7† | <1.5 ± 0.0 |
| Placebo | 6/10 (60) | 14.8 ± 4.0 | 8/10 (80) | 5.0 ± 2.3 | 3.1 ± 1.4 | 1.6 ± 0.3 | a The vaccine was administered intramuscularly 11 and 4 weeks prior to virus challenge.
b Log10 cell culture infections doses per ml, determined from vaginal swabs.
c After virus inoculation.
* P<0.001.
† P=0.08, ∅ P=0.06.

FIG. 8

POLYNUCLEOTIDE HERPES VIRUS VACCINE

This application is a continuation of application Ser. No. 08/720,758, filed Oct. 1, 1996, now abandoned, which is a continuation-in-part of application Ser. No. 08/715,309, filed Sep. 18, 1996, now abandoned, which is a continuation of application Ser. No. 08/279,459, filed Jul. 22, 1994, now abandoned.

BACKGROUND OF THE INVENTION

A major obstacle to the development of vaccines against viruses, particularly those with multiple serotypes or a high rate of mutation, against which elicitation of neutralizing and protective immune responses is desirable, is the diversity of the viral external proteins among different viral isolates or strains. Since cytotoxic T-lymphocytes (CTLs) in both mice and humans are capable of recognizing epitopes derived from conserved internal viral proteins [J. W. Yewdell et al., *Proc. Natl. Acad. Sci. (USA)* 82, 1785 (1985); A. R. M. Townsend, et al., *Cell* 44, 959 (1986); A. J. McMichael et al., *J. Gen. Virol.* 67, 719 (1986); J. Bastin et al., *J. Exp. Med.* 165, 1508 (1987); A. R. M. Townsend and H. Bodmer, *Annu. Rev. Immunol.* 7, 601 (1989)], and are thought to be important in the immune response against viruses [Y.-L. Lin and B. A. Askonas, *J. Exp. Med.* 154, 225 (1981); I. Gardner et al., *Eur. J. Immunol.* 4, 68 (1974); K. L. Yap and G. L. Ada, *Nature* 273, 238 (1978); A. J. McMichael et al., *New Engl. J. Med.* 309, 13 (1983); P. M. Taylor and B. A. Askonas, *Immunol.* 58, 417 (1986)], efforts have been directed towards the development of CTL vaccines capable of providing heterologous protection against different viral strains.

It is known that CTLs kill virally-infected cells when their T cell receptors recognize viral peptides associated with MHC class I and or class II molecules. These peptides can be derived from endogenously synthesized viral proteins, regardless of the protein's location or function within the virus. By recognition of epitopes from conserved viral proteins, CTLs may provide heterologous protection.

Many infectious disease causing agents can, by themselves, elicit protective antibodies which can bind to and kill, render harmless, or cause to be killed or rendered harmless, the disease causing agent and its byproducts. Recuperation from these diseases usually results in long-lasting immunity by virtue of protective antibodies generated against the highly antigenic components of the infectious agent.

Protective antibodies are part of the natural defense mechanism of humans and many other animals, and are found in the blood as well as in other tissues and bodily fluids. It is the primary function of most vaccines to elicit protective antibodies against infectious agents and/or their byproducts, without causing disease.

Most efforts to generate CTL responses have either used replicating vectors to produce the protein antigen within the cell [J. R. Bennink et al., *ibid.* 311, 578 (1984); J. R. Bennink and J. W. Yewdell, *Curr. Top. Microbiol. Immunol.* 163, 153 (1990); C. K. Stover et al., *Nature* 351, 456 (1991); A. Aldovini and R. A. Young, *Nature* 351, 479 (1991); R. Schafer et al., *J. Immunol.* 149, 53 (1992); C. S. Hahn et al., *Proc. Natl. Acad. Sci. (USA)* 89, 2679 (1992)], or they have focused upon the introduction of peptides into the cytosol [F. R. Carbone and M. J. Bevan, *J. Exp. Med.* 169, 603 (1989); K. Deres et al., *Nature* 342, 561 (1989); H. Takahashi et al., *ibid.* 344, 873 (1990); D. S. Collins et al., *J. Immunol.* 148, 3336 (1992); M. J. Newman et al., *ibid.* 148, 2357 (1992)]. Both of these approaches have limitations that may reduce their utility as vaccines. Retroviral vectors have restrictions on the size and structure of polypeptides that can be expressed as fusion proteins while maintaining the ability of the recombinant virus to replicate [A. D. Miller, *Curr. Top. Microbiol. Immunol.* 158, 1 (1992)], and the effectiveness of vectors such as vaccinia for subsequent immunizations may be compromised by immune responses against vaccinia [E. L. Cooney et al., *Lancet* 337, 567 (1991)]. Also, viral vectors and modified pathogens have inherent risks that may hinder their use in humans [R. R. Redfield et al., *New Engl. J. Med.* 316, 673 (1987); L. Mascola et al., *Arch. Intern. Med.* 149, 1569 (1989)]. Furthermore, the selection of peptide epitopes to be presented is dependent upon the structure of an individual's MHC antigens and, therefore, peptide vaccines may have limited effectiveness due to the diversity of MHC haplotypes in outbred populations.

Benvenisty, N., and Reshef, L. [*PNAS* 83, 9551–9555, (1986)] showed that $CaCl_2$ precipitated DNA introduced into mice intraperitoneally (i.p.), intravenously (i.v.) or intramuscularly (i.m.) could be expressed. The intramuscular (i.m.) injection of DNA expression vectors in mice has been demonstrated to result in the uptake of DNA by the muscle cells and expression of the protein encoded by the DNA [J. A. Wolff et al., *Science* 247, 1465 (1990); G. Ascadi et al., *Nature* 352, 815 (1991)]. The plasmids were shown to be maintained episomally and did not replicate. Subsequently, persistent expression has been observed after i.m. injection in skeletal muscle of rats, fish and primates, and cardiac muscle of rats [H. Lin et al., *Circulation* 82, 2217 (1990); R. N. Kitsis et al., *Proc. Natl. Acad. Sci. (USA)* 88, 4138 (1991); E. Hansen et al., *FEBS Lett.* 290, 73 (1991); S. Jiao et al., *Hum. Gene Therapy* 3, 21 (1992); J. A. Wolff et al., *Human Mol. Genet.* 1, 363 (1992)]. The technique of using nucleic acids as therapeutic agents was reported in WO90/11092 (Oct. 4, 1990), in which naked polynucleotides were used to vaccinate vertebrates.

Recently, the coordinate roles of B7 and the major histocompatibility complex (MHC) presentation of epitopes on the surface of antigen presenting cells in activating CTLs for the elimination of tumors was reviewed [Edgington, *Biotechnology* 11, 1117–1119, 1993]. Once the MHC molecule on the surface of an antigen presenting cell (APC) presents an epitope to a T-cell receptor (TCR), B7 expressed on the surface of the same APC acts as a second signal by binding to CTLA-4 or CD28. The result is rapid division of $CD4^+$ helper T-cells which signal $CD8^+$ T-cells to proliferate and kill the APC.

It is not necessary for the success of the method that immunization be intramuscular. Thus, Tang et al., [*Nature*, 356, 152–154 (1992)] disclosed that introduction of gold microprojectiles coated with DNA encoding bovine growth hormone (BGH) into the skin of mice resulted in production of anti-BGH antibodies in the mice. Furth et al., [*Analytical Biochemistry*, 205, 365–368, (1992)] showed that a jet injector could be used to transfect skin, muscle, fat, and mammary tissues of living animals. Various methods for introducing nucleic acids was recently reviewed [Friedman, T., *Science*, 244, 1275–1281 (1989)]. See also Robinson et al., [*Abstracts of Papers Presented at the* 1992 *meeting on Modern Approaches to New Vaccines, Including Prevention of AIDS*, Cold Spring Harbor, p92], where the im, ip, and iv administration of avian influenza DNA into chickens was alleged to have provided protection against lethal challenge. Intravenous injection of a DNA: cationic liposome complex in mice was shown by Zhu et al., [*Science* 261, 209–211 (Jul.

9, 1993); see also WO93/24640, Dec. 9, 1993] to result in systemic expression of a cloned transgene. Recently, Ulmer et al., [*Science* 259, 1745–1749, (1993)] reported on the heterologous protection against influenza virus infection by injection of DNA encoding influenza virus proteins.

Wang et al., [*P.N.A.S. USA* 90, 4156–4160 (May, 1993)] reported on elicitation of immune responses in mice against HIV by intramuscular inoculation with a cloned, genomic (unspliced) HIV gene. However, the level of immune responses achieved was very low, and the system utilized portions of the mouse mammary tumor virus (MMTV) long terminal repeat (LTR) promoter and portions of the simian virus 40 (SV40) promoter and terminator. SV40 is known to transform cells, possibly through integration into host cellular DNA. Thus, the system described by Wang et al., is wholly inappropriate for administration to humans, which is one of the objects of the instant invention.

WO 93/17706 describes a method for vaccinating an animal against a virus, wherein carrier particles were coated with a gene construct and the coated particles are accelerated into cells of an animal.

Recent efforts to develop subunit vaccines for herpes simplex virus (HSV) have focused on novel expression and presentation of viral antigens; especially the viral glycoproteins. [for review see Burke, R. L., 1993, Sem. In Virol., 4, pp.187–197] Recombinant HSV glycoproteins expressed by a variety of systems including yeast (Kino., Y. C. et al., 1989, Vaccine, 7, pp.155–160), insect cells (Ghiasi, H. et al., 1991, Arch.Virol., 121, pp.163–178), and mammalian cells (Burke, R. L., 1991, Rev.Infect.Dis., 13 S906–S911; Lasky, L. A., 1990, J.Med.Virol., 31, pp.59–61) have been shown to elicit protective immunity in animal models. Clinical trials of a recombinant HSV-2 glycoprotein D (gD) produced in Chinese hamster ovary cells have shown that the vaccine induces an antibody response in naive individuals and stimulates the pre-existing response in both HSV-1 and HSV-2 seropositive individuals. (Straus, S. E. et al., 1993, J.Infect.Dis., 167, pp.1045–1052)

An alternate approach to subunit vaccination has been the use of live virus vectors for delivery of HSV antigens. Vaccinia-HSV recombinants expressing gD (Aurelian, L. et al., 1991, Rev.Infect.Dis., 13, S924–S930; Rooney, J. F. et al., 1991, Rev.Infect.Dis., 13, S898–S903; Wachsman, M. et al., 1992, Vaccine, 10, pp.447–454) gB (Rooney, J. F. et al., supra), gL and gH (Browne, H. et al., 1993, J.Gen.Virol., 74, pp.2813–2817) have successfully protected animals from HSV challenge. Vaccination by infection with recombinant adenovirus expressing HSV gB elicits a protective immune response in mice. (Ghiasi, H., supra; McDermott, M. R., 1989, Virology, 169, pp.244–247) It is well documented that anti-gD antibodies can protect against HSV infection whether elicited by immunization with native protein (Long, D. et al., 1984, Infect.Immun., 43, pp.761–764) recombinantly expressed protein (Burke, R. L., supra; Stanberry, L. R. et al., 1987, J.Infect.Dis., 155, pp.914–920; Straus, S.E., supra) peptides derived from gD (Eisenberg, R. J. et al., 1985, J.Virol., 56, pp.1014–1027) or transferred passively (Dix, R. D. et al., 1981, Infect.Immun., 34, pp.192–199; Ritchie, M. H. et al., 1993, Investigative Ophthalmology and Visual Sciences, 34, pp.2460–2468).

Studies by Wolff et al. (supra) originally demonstrated that intramuscular injection of plasmid DNA encoding a reporter gene results in the expression of that gene in myocytes, at and near the sight of injection. Recent reports demonstrated the successful immunization of mice against influenza by the injection of plasmids encoding influenza A hemagglutinin (Montgomery, D. L. et al., 1993, Cell Biol., 12, pp.777–783), or nucleoprotein (Montgomery, D. L. et al., supra; Ulmer, J. B. et al., 1993, Science, 259, pp.1745–1749). The first use of DNA immunization for a herpes virus has been reported (Cox et al., 1993, J.Virol., 67, pp.5664–5667). Injection of a plasmid encoding bovine herpesvirus 1 (BHV-1) glycoprotein g IV gave rise to anti-g IV antibodies in mice and calves. Upon intranasal challenge with BHV-1, immunized calves showed reduced symptoms and shed substantially less virus than controls. The ability of HSV glycoprotein D to elicit a protective immune response in mice (Long, D. et al., supra) and guinea pigs (Stanberry, L. R. et al., supra; Stanberry, L. R. et al., 1989, Antiviral.Res., 11, pp.203–214) is well documented.

SUMMARY OF THE INVENTION

To test the efficacy of DNA immunization in the prevention of HSV disease, HSV-2 protein-coding DNA sequences were cloned into the eukaryotic expression vector. This DNA construction elicits an immune response when injected into animals. Immunized animals were infected with HSV to evaluate whether or not direct DNA immunization with the gD gene (or other HSV-2 genes) could protect them from disease. Nucleic acids, including DNA constructs and RNA transcripts, capable of inducing in vivo expression of human herpes simplex virus (HSV) proteins upon direct introduction into animal tissues via injection or otherwise are therefore disclosed. Injection of these nucleic acids may elicit immune responses which result in the production of cytotoxic T lymphocytes (CTLs) specific for HSV antigens, as well as the generation of HSV-specific antibodies, which are protective upon subsequent HSV challenge. These nucleic acids are useful as vaccines for inducing immunity to HSV, which can prevent infection and/or ameliorate HSV-related disease.

In a particular embodiment of the present invention DNA vaccines expressing herpes simplex virus type 2 (HSV-2) full-length glycoprotein D (gD), or a truncated form of HSV-2 glycoprotein B (gB) are used to provide for protective efficacy against HSV-2 infection.

The present invention also relates to use of plasmid expression vectors encoding herpes simplex virus type 2 (HSV-2) proteins for their ability to immunize a host against a herpes infection. The protein may be expressed along or in combination with one or more additional proteins which will induce an immune response to HSV.

In a preferred embodiment of the present invention, full-length glycoprotein D (gD), and a truncated form of HSV-2 glycoprotein B (gB) are used in a low-dosage form as a combination vaccine preparation.

In a preferred embodiment of the present invention, immunization with a plasmid expressing the amino-terminal 707 amino acids (aa) of gB is used to induce a humoral immune response detected by ELISA and virus neutralization.

In an especially preferred aspect of the present invention, a truncated gB plasmid is combined with a plasmid expressing full-length gD. This combinantion of DNA constructs may be in the form of distinct DNA vectors, or a single vector which expresses each antigenic protein or protein fragment. Again, these nucleic acid constructs are useful as vaccines for inducing immunity to HSV, which can prevent infection and/or ameliorate HSV-related disease.

Figure 1A:
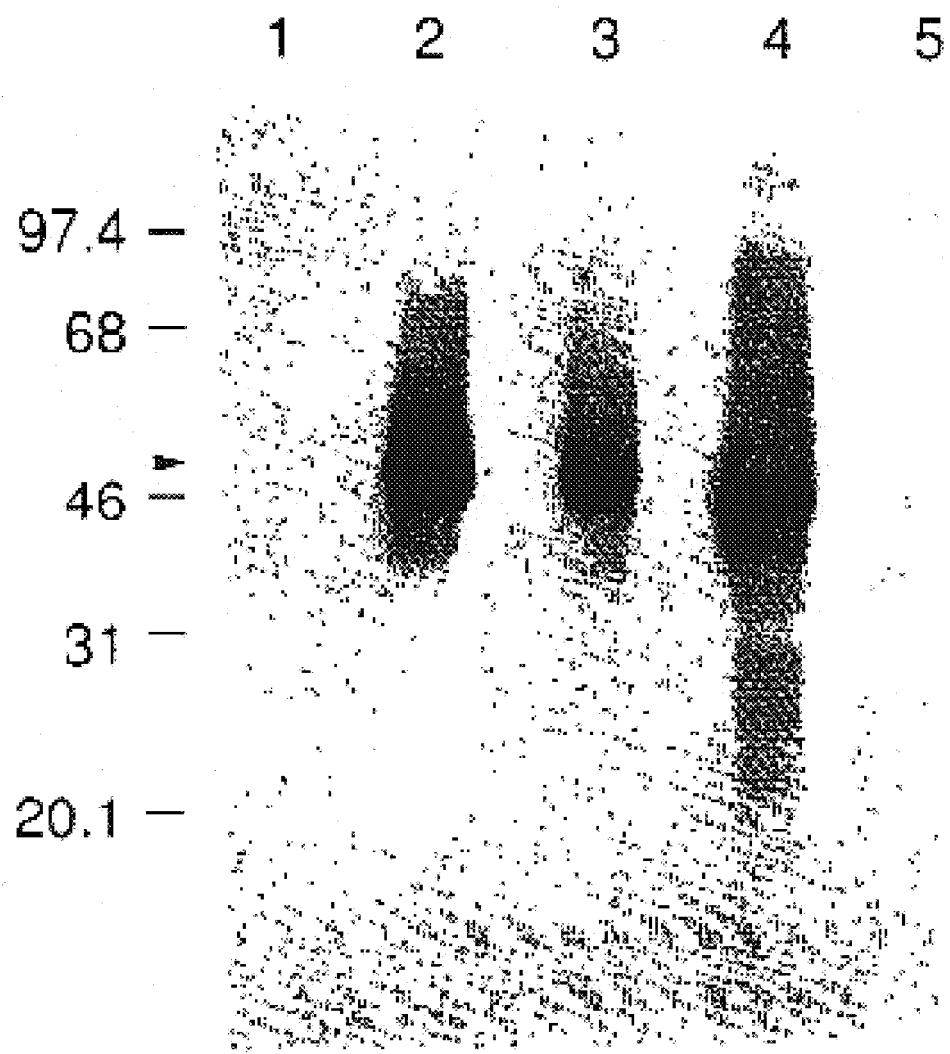
FIG. 1. Panels A, B, and C
A. Western blot analysis of HSV gD expression by V1J:gD-transfected cells is shown;
1. mock infected Vero cells;
2. HSV-2 186 infected Vero cells (moi=1);
3. HSV-2 Curtis infected Vero cells (moi=1);
4. RD cells transfected with V1J:gD;
5. mock transfected RD cells.

B. Western blot analysis of HSV gB expression by V1JNS:gB-transfected cells is shown.
C. Western blot analysis of HSV ICP27 expression by V1J:ICP27-transfected cells is shown.
Figure 1B:
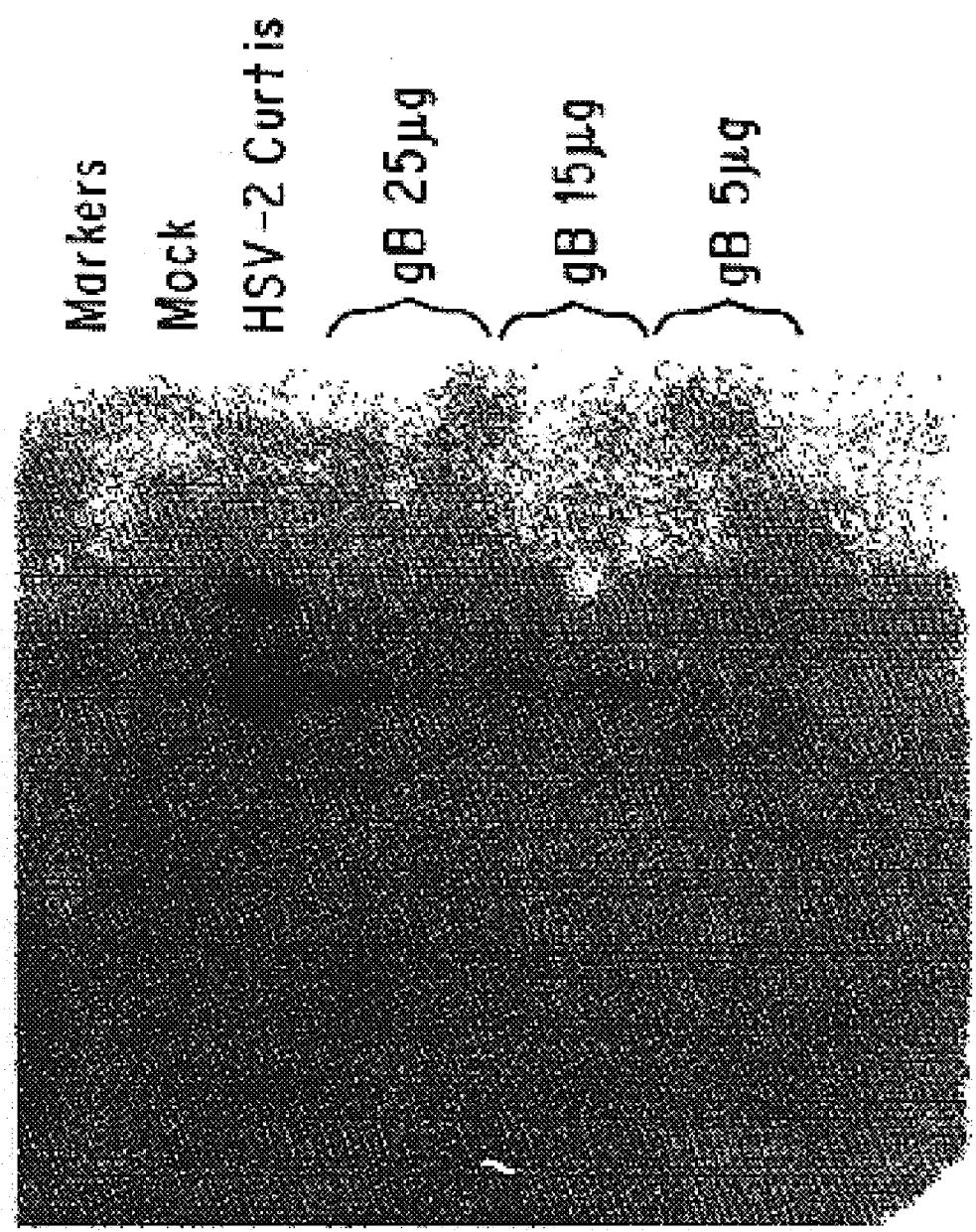
Figure 1C:
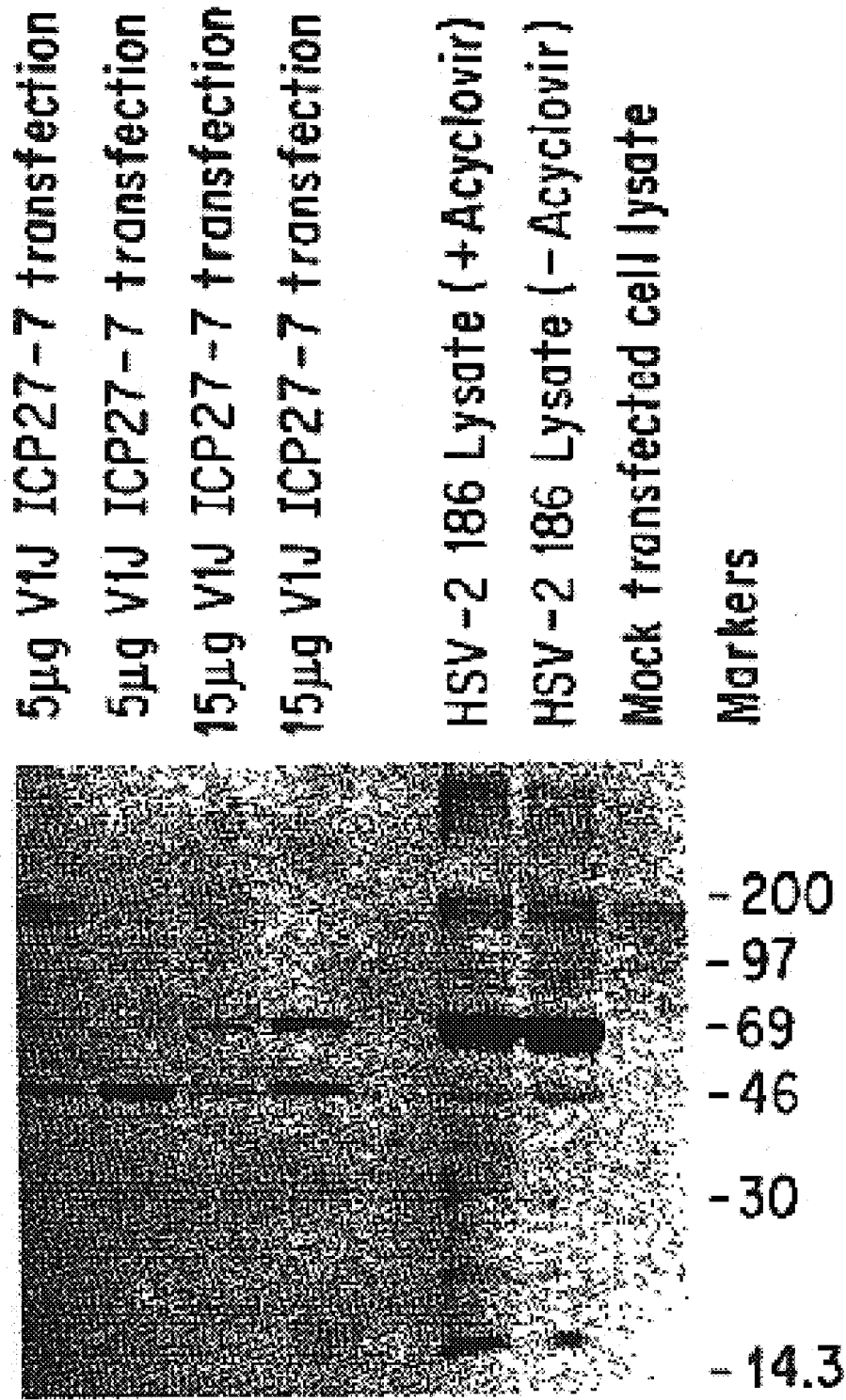

FIG. 5. Survival of HSV-2 challenged animals following one injection with V1J:gD at 50 ug; 16.7 ug; 5.0 ug; 1.67 ug; 0.5 ug; 0.167 ug; 0.05 ug; 0.017 ug; 0.005 ug; or saline only.

FIG. 6. Survival of animals immunized with V1JNS:gB following HSV challenge is shown.

FIG. 7 Survival of animals immunized with V1J:gC following HSV challenge is shown.

FIG. 8 The results of survival, mean days to death, paralysis, and vaginal virus titers in HSV-2 infected guinea pigs is shown.

FIG. 9 Guinea pig vaginal lesion scores are shown.

FIG. 10 The effect of DNA immunization on the survival of mice infected by i.p. injection with HSV-2 in Example 11 is shown. Mice were immunized twice with gD-2 (A) in a two-fold dilution series, or with ΔgB-2 (B) in a half-log dilution series, or with saline. The doses (μg) are indicated on the figure. The numbers of mice in each group are noted in Table 8. Mice were challenged by i.p. injection with 0.25 mL ($10^{5.7}$ pfu) of a clarified stock of HSV-2 strain Curtis, and were observed for three weeks for signs of disease and survival.

FIG. 11. The effect of immunization with gD-2 DNA or vector DNA on the survival of mice infected by i.p. injection with HSV-2 is shown. Mice were immunized with 12.5 μg (o), 1.6 μg gD-2 (•), or with 12.5 μg (o) vector V1J. Viral challenge was as described in FIG. 10.

FIG. 12 The effect of immunization with gD-2 and ΔgB-2 DNA in combination on primary HSV-2-induced genital disease in guinea pigs is shown for Example 11. Immunized and sham-immunized guinea pigs were infected by application of HSV-2 strain MS to the vagina and external genital skin. One hour prior to infection, the vaginal closure membrane was ruptured with a saline moistened cotton swab; the vagina and external skin were then swabbed with 0.1 N NaOH. Virus was introduced using a cotton swap dipped into a clarified HSV-2 MS-infected Vero cell lysate diluted in tissue culture medium to $10^{6.7}$ pfu/mL. The swab was inserted into the vagina, twisted back and forth five times then removed and wiped over the external genitalia. To ensure infection, virus application was repeated one hour later. For the mock-infected group, the inoculum was prepared from mock-infected Vero cells. Animals were caged randomly and evaluated daily by observers blinded to the study groups. On day three, the vagina was swabbed with a moistened calcium alginate swab which was eluted into 2 mL of virus transport medium (Carr-Scarborough Microbiologicals Inc.; Stone Mt., Ga.). Infection was confirmed by reisolation of virus, a positive response in the HERPCHEK™ kit (Dupont, North Billerica, Mass.), or appearance of symptomatic disease, and the development of antibodies to nonstructural HSV proteins. The severity of external disease was quantified using a visual scoring system adapted from that described by Stanberry, et al. (1982*, J. Infect. Dis*. 146: 397–404). Numerical scores were assigned to specific disease signs using the following scale: 0, no disease; 1, redness or swelling; 2, several (≦3) small vesicles; 3, several (≦3) large vesicles; 4, large ulcers with maceration. Scores of 0.5, 1.5, 2.5, and 3.5 were assigned to disease of intermediate severity. Daily mean lesion scores were calculated by dividing the sum of a group's lesion scores by the number of observations. In the case of death during the observation period, the final score assigned to that animal was carried through to the end of the observation period. Animals were immunized with 3 μg gD-2+10 μg ΔgB-2 and challenged with HSV-2 (o) n=7; sham-immunized with saline and challenged with HSV-2 (o) n=8; or sham-immunized and mock-infected (t) n=6. *three animals euthanized, † two animals euthanized.

FIGS. 13A and B. Effect of immunization with V1Jns:ΔgB on HSV-induced disease in guinea pigs is shown for Example 12. Immunized animals were challenged and evaluated essentially as described by Stanberry, et al., (id.). One hour after rupturing the vaginal closure membrane with a moistened cotton swab, $10^{5.7}$ pfu of HSV-2 strain MS were delivered into the vagina with a gavage needle. Infection was confirmed by reisolation of virus from the vagina at days 2 or 4, with the HERPCHEK™ kit (DuPont), or by evaluation of post-challenge sera. Animals were caged randomly and evaluated by observers blinded to the study groups. Numerical scores were assigned to specific disease signs using the following scale: 0, no disease; 1, redness or swelling; 2, several (≦3) small vesicles; 3, several (≦3) large vesicles; 4, large ulcers with maceration. Scores of 0.5, 1.5, 2.5, and 3.5 were assigned to disease of intermediate severity. Daily mean lesion scores were calculated by dividing the sum of a group's lesion scores by the number of observations. In the case of death during the primary phase of disease, the last score assigned to that animal was carried through to the end of the observation period. (A) primary disease. Δ, 100 μg V1Jns:HA (n=10); n, 10 μg V1Jns:ΔgB (n=9); 1, 100 μg V1Jns:ΔgB (n=9). (B) recurrent disease. Δ, 100 μg V1Jns:HA (n=6); n, 10 μg V1Jns:ΔgB (n=7); 1, 100 μg V1Jns:ΔgB (n=9).

FIGS. 14A and B Effect of immunization with V1Jns:ΔgB+V1Jns:gD on HSV-induced disease in guinea pig for Example 12 is shown. Viral challenge and disease evaluation were as described in FIG. 1. (A) primary disease. Δ, 100 μg V1Jns:HA (n=8); 1, 100 μg V1Jns:ΔgB+100 μg V1Jns:gD (n=8). (B) recurrent disease. Δ, 100 μg V1Jns:HA (n=8); 1, 100 μg V1Jns:ΔgB+100 μg V1Jns:gD (n=8).

FIG. 15 Groups of six African green monkeys were immunized with DNA mixtures containing 100 or 10 μg each, of gD and gB DNA (see Example 11 and 12) at 0 and 4 weeks, and were boosted at 24 weeks. Sera obtained at four-week intervals were analyzed for anti-gD and anti-gB antibodies with antigen-specific ELISAS. For neutralization titers, the percent plaque reduction was determined (in duplicate) for each serum diiution compared to the same dilution of preimmune serum, scoring a 50% or greater reduction in plaque number as positive. Ten-fold serial dilutions ranging from 1:10 to 1:10,000 were assayed; endpoint titers were calculated by, linear regression analysis. (Sera negative at the lowest dilution tested were assigned endpoint titers of 1.) Arrows indicate immunization. (A) ELISA $\log_{10}$ GMT +/− the standard error. anti-gD response: Δ, 100 μg-dose group; ▲ 104 μ-dose group. anti-gB response: q 100 μg dose group; n 104 μg-dose group. (B) GMT +/− SE HSV-2 neutralizing antibodies. m 100 μg-dose group; 110 μg-dose group.

DETAILED DESCRIPTION OF THE INVENTION

This invention provides polynucleotides which, when directly introduced into a vertebrate in vivo, including mammals such as humans, induces the expression of encoded proteins within the animal. As used herein, a polynucleotide is a nucleic acid which contains essential regulatory elements such that upon introduction into a living vertebrate cell, is able to direct the cellular machinery to produce translation products encoded by the genes comprising the polynucleotide. In one embodiment of the invention, the polynucleotide is a polydeoxyribonucleic acid comprising HSV genes operatively linked to a transcriptional promoter. In another embodiment of the invention the polynucleotide vaccine comprises polyribonucleic acid encoding HSV genes which are amenable to translation by the eukaryotic cellular machinery (ribosomes, tRNAs, and other translation factors). Where the protein encoded by the polynucleotide is one which does not normally occur in that animal except in pathological conditions, (i.e. an heterologous protein) such as proteins associated with HSV, the animals' immune system is activated to launch a protective immune response. Because these exogenous proteins are produced by the animals' own tissues, the expressed proteins are processed by the major histocompatibility system (MHC) in a fashion analogous to when an actual HSV infection occurs. The result, as shown in this disclosure, is induction of immune responses against HSV. Polynucleotides for the purpose of generating immune responses to an encoded protein are referred to herein as polynucleotide vaccines or PNV.

There are many embodiments of the instant invention which those skilled in the art can appreciate from the specification. Thus, different transcriptional promoters, terminators, carrier vectors or specific gene sequences may be used successfully.

The instant invention provides a method for using a polynucleotide which, upon introduction into mammalian tissue, induces the expression, in vivo, of the polynucleotide thereby producing the encoded protein. It is readily apparent to those skilled in the art that variations or derivatives of the nucleotide sequence encoding a protein can be produced which alter the amino acid sequence of the encoded protein. The altered expressed protein may have an altered amino acid sequence, yet still elicits antibodies which react with the viral protein, and are considered functional equivalents. In addition, fragments of the full length genes which encode portions of the full length protein may also be constructed. These fragments may encode a protein or peptide which elicits antibodies which react with the viral protein, and are considered functional equivalents.

In one embodiment of this invention, a gene encoding an HSV gene product is incorporated in an expression vector. The vector contains a transcriptional promoter recognized by eukaryotic RNA polymerase, and a transcriptional terminator at the end of the HSV gene coding sequence. In a preferred embodiment, the promoter is the cytomegalovirus promoter with the intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator. The combination of CMVintA-BGH terminator is preferred. In addition, to assist in preparation of the polynucleotides in prokaryotic cells, an antibiotic resistance marker is also optionally included in the expression vector under transcriptional control of a suitable prokaryotic promoter. Ampicillin resistance genes, neomycin resistance genes or any other suitable antibiotic resistance marker may be used. In a preferred embodiment of this invention, the antibiotic resistance gene encodes a gene product for neomycin resistance. Further, to aid in the high level production of the polynucleotide by growth in prokaryotic organisms, it is advantageous for the vector to contain a prokaryotic origin of replication and be of high copy number. Any of a number of commercially available prokaryotic cloning vectors provide these elements. In a preferred embodiment of this invention, these functionalities are provided by the commercially available vectors known as the pUC series. It may be desirable, however, to remove non-essential DNA sequences. Thus, the lacZ and lacI coding sequences of pUC may be removed. It is also desirable that the vectors are not able to replicate in eukaryotic cells. This minimizes the risk of integration of polynucleotide vaccine sequences into the recipients' genome.

In another embodiment, the expression vector pnRSV is used, wherein the rous sarcoma virus (RSV) long terminal repeat (LTR) is used as the promoter. In yet another embodiment, V1, a mutated pBR322 vector into which the CMV promoter and the BGH transcriptional terminator were cloned is used. In a preferred embodiment of this invention, the elements of V1 and pUC19 have been been combined to produce an expression vector named V1J. Into V1J or another desirable expression vector is cloned an HSV gene, such as gD, or any other HSV gene which can induce anti-HSV immune responses (antibody and/or CTLs) such as gB, gC, gL, gH and ICP27. In another embodiment, the ampicillin resistance gene is removed from V1J and replaced with a neomycin resistance gene, to generate V1J-neo, into which any of a number of different HSV genes may be cloned for use according to this invention. In yet another embodiment, the vector is V1Jns, which is the same as V1Jneo except that a unique Sfi1 restriction site has been engineered into the single Kpn1 site at position 2114 of V1J-neo. The incidence of Sfi1 sites in human genomic DNA is very low (approximately 1 site per 100,000 bases). Thus, this vector allows careful monitoring for expression vector integration into host DNA, simply by Sfi1 digestion of extracted genomic DNA. In a further embodiment, the vector is V1R. In this vector, as much non-essential DNA as possible is "trimmed" to produce a highly compact vector. This vector allows larger inserts to be used, with less concern that undesirable sequences are encoded and optimizes uptake by cells when the construct encoding specific virus genes is introduced into surrounding tissue. The methods used in producing the foregoing vector modifications and development procedures may be accomplished according to methods known by those skilled in the art.

From this work those skilled in the art will recognize that one of the utilities of the instant invention is to provide a system for in vivo as well as in vitro testing and analysis so that a correlation of HSV sequence diversity with serology of HSV neutralization, as well as other parameters can be made. The isolation and cloning of these various genes may be accomplished according to methods known to those skilled in the art. This invention further provides a method for systematic identification of HSV strains and sequences for vaccine production. Incorporation of genes from primary isolates of HSV strains provides an immunogen which induces immune responses against clinical isolates of the virus and thus meets a need as yet unmet in the field. Furthermore, if the virulent isolates change, the immunogen may be modified to reflect new sequences as necessary.

In one embodiment of this invention, a gene encoding an HSV protein is directly linked to a transcriptional promoter. The use of tissue-specific promoters or enhancers, for example the muscle creatine kinase (MCK) enhancer element may be desirable to limit expression of the polynucleotide to a particular tissue type. For example, myocytes are terminally differentiated cells which do not divide. Integration of foreign DNA into chromosomes appears to require both cell division and protein synthesis. Thus, limiting protein expression to non-dividing cells such as myocytes may be preferable. However, use of the CMV promoter is adequate for achieving expression in many tissues into which the PNV is introduced.

PNV Construct Summary

HSV and other genes are preferably ligated into an expression vector which has been specifically optimized for polynucleotide vaccinations. Elements include a transcriptional promoter, immunogenic epitopes, and additional cistrons encoding immunoenhancing or immunomodulatory genes, with their own promoters, transcriptional terminator, bacterial origin of replication and antibiotic resistance gene, as described herein. Optionally, the vector may contain internal ribosome entry sites (IRES) for the expression of polycistronic mRNA. Those skilled in the art will appreciate that RNA which has been transcribed in vitro to produce multi-cistronic mRNAs encoded by the DNA counterparts is within the scope of this invention. For this purpose, it is desirable to use as the transcriptional promoter such powerful RNA polymerase promoters as the T7 or SP6 promoters, and performing run-on transcription with a linearized DNA template. These methods are well known in the art.

The protective efficacy of polynucleotide HSV immunogens against subsequent viral challenge is demonstrated by immunization with the DNA of this invention. This is advantageous since no infectious agent is involved, no assembly of virus particles is required, and determinant selection is permitted. Furthermore, because the sequence of viral gene products may be conserved among various strains of HSV, protection against subsequent challenge by another strain of HSV is obtained.

The injection of a DNA expression vector encoding gD may result in the generation of significant protective immunity against subsequent viral challenge. In particular, gD-specific antibodies and CTLs may be produced. Immune responses directed against conserved proteins can be effective despite the antigenic shift and drift of the variable proteins. Because each of the HSV gene products exhibit some degree of conservation among the various strains of HSV, and because immune responses may be generated in response to intracellular expression and MHC processing, it is expected that many different HSV gD PNV constructs may give rise to cross reactive immune responses.

The invention offers a means to induce heterologous protective immunity without the need for self-replicating agents or adjuvants. The generation of high titer antibodies against expressed proteins after injection of viral protein and human growth hormone DNA, [Tang et al., Nature 356, 152, 1992], indicates this is a facile and highly effective means of making antibody-based vaccines, either separately or in combination with cytotoxic T-lymphocyte vaccines targeted towards conserved antigens.

The ease of producing and purifying DNA constructs compares favorably with traditional protein purification, facilitating the generation of combination vaccines. Thus, multiple constructs, for example encoding gD and any other HSV gene also including non-HSV genes may be prepared, mixed and co-administered. Additionally, protein expression is maintained following DNA injection [H. Lin et al., Circulation 82, 2217 (1990); R. N. Kitsis et al., Proc. Natl. Acad. Sci. (USA) 88, 4138 (1991); E. Hansen et al., FEBS Lett. 290, 73 (1991); S. Jiao et al., Hum. Gene Therapy 3, 21 (1992); J. A. Wolff et al., Human Mol. Genet. 1, 363 (1992)], the persistence of B- and T-cell memory may be enhanced [D. Gray and P. Matzinger, J. Exp. Med. 174, 969 (1991); S. Oehen et al., ibid. 176, 1273 (1992)], thereby engendering long-lived humoral and cell-mediated immunity.

The amount of expressible DNA or transcribed RNA to be introduced into a vaccine recipient will depend on the strength of the transcriptional and translational promoters used. The magnitude of the immune response may depend on the level of protein expression and on the immunogenicity of the expressed gene product. In general, an effective dose of about 1 ng to 5 mg, and preferably about 10 µg to 300 µg is administered directly into muscle tissue. Subcutaneous injection, intradermal introduction, impression through the skin, and other modes of administration such as intraperitoneal, intravenous, or inhalation delivery are also suitable. It is also contemplated that booster vaccinations may be provided. Following vaccination with HSV polynucleotide immunogen, boosting with HSV protein immunogens such as the gD, gB, gC, gG, and gH gene products is also contemplated. Parenteral administration, such as intravenous, intramuscular, subcutaneous or other means of administration of interleukin-12 protein, concurrently with or subsequent to parenteral introduction of the PNV of this invention may be advantageous.

The polynucleotide may be naked, that is, unassociated with any proteins, adjuvants or other agents which affect the recipients' immune system. In this case, it is desirable for the polycucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

In another embodiment, the invention is a polynucleotide which comprises contiguous nucleic acid sequences capable of being expressed to produce a gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode a human herpes simplex virus immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to insure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a $CD8^+$ response to NP that protected mice against challenge with heterologous strains of flu. (Montgomery, D. L. et al., supra; Ulmer, J. et al., supra)

There is evidence that cell-mediated immunity is important in controlling HSV infection [for review see Nash, A. A. et al., 1985, In: The Herpesviruses, Vol.4, Plenum, New York, and Schmidt, D. S. et al., 1992, In: Rouse (ed.), Current Topics In Microbiology And Immunology, Vol.179, Herpes Simplex Virus; Pathogenesis, immunobiology and Control, Springer-Verlag, Berlin]. While the majority of HSV CTLs isolated from HSV seropositive patients are of the $CD4^+$ type (Schmidt, D. S. et al., 1988, J.Immunol., 140, pp.3610–3616; Tsutsumi, T. et al., 1986, Clin.Exp.immunol., 66, pp.507–515) $CD8^+$ clones, including one specific for gD, have been isolated. (Torpey, D. J. et al., 1989, J.Immunol., 142, pp.1325–1332; Yasukawa, M. et al., 1989, J.Immunol., 143, pp.2051–2057; Zarling, J. M. et al., 1986, J.Immunol., 136 pp.4669–4673) In mice, cell transfer and depletion experiments suggest that some $CD8^+$ CTLs protect against infection. (Bonneua, R. H. et al., 1989, J.Virol, 63, pp.1480–1484; Nash, A. A. et al., 1987, J.Gen.Virol., 68, pp.825–833) Immunization with gD via infection with recombinant virus vectors (Paoletti, E. et al., 1984, Proc.Natl.Acad. Sci. USA, 81, pp.193–197; Wachsman, M. L. et al., 1987, J.Infect.Dis., 155, pp.1188–1197; Zheng, B. et al., 1993, Vaccine, 11, pp.1191–1198) protects mice from HSV infection. Live virus vectors, like DNA, have the potential for MHC class I presentation of the immunogen. However, a recent study using infection by an HSV gD-vaccinia recombinant to immunize mice found that protection from challenge was dependent on the delayed type hypersensitivity functions of $L3T4^+$ cells. (Wachsman, M. et al., 1992, Vaccine, 10, pp.447–454) Although, gD-specific $CD8^+$ cells have been isolated from HSV infected mice, their role in limiting infection is unknown. (Johnson, R. M. et al., 1990, J.Immunol., 145, pp.702–710) Work by Koelle et al., suggests that HSV infection of human fibroblasts and keratinocytes may render them unrecognizable to $CD8^+$ CTLs (Koelle, D. M. et al., 1993, J.Clin.Invest., 91, pp.961–968). In natural HSV infection, the role of $CD8^+$ cells in general, and the role of $CD8^+$ response to gD in particular is not resolved.

Since DNA immunization can evoke both humoral and cell-mediated immune responses, its greatest advantage may be that it provides a relatively simple method to survey a large number of viral genes for their vaccine potential. Plasmids expressing HSV-2 glycoproteins B and C also elicit neutralizing antibodies and protect mice from lethal challenge. However, ICP27 which is known to generate a CTL response and to provide some protection in mice immunized by infection with ICP27-vaccinia recombinant virus (Banks, T. A. et al., 1991, J.Virol., 65, pp.3185–3191) did not provide protection from lethal HSV challenge when mice were vaccinated with PNV ICP27 alone. However, ICP27-encoding DNA may be useful as one component of a multi-HSV gene-containing PNV, and it is contemplated that the present invention includes ICP27 as a component of a multivalent HSV PNV.

Immunization by DNA injection also allows, as discussed above, the ready assembly of multicomponent subunit vaccines. Simultaneous immunization with multiple influenza genes has recently been reported. (Donnelly, J. et al., 1994, Vaccines, in press). The inclusion in an HSV vaccine of genes whose products activate different arms of the immune system may also provide thorough protection from subsequent virus challenge.

In a particular embodiment of the present invention DNA vaccines expressing herpes simplex virus type 2 (HSV-2) full-length glycoprotein D (gD), or a truncated form of HSV-2 glycoprotein B (gB) are used to provide for protective efficacy in two experimental models of HSV-2 infection. This particular embodiment of the present invention discloses intramuscular (i.m.) injection of mice with subsequent induction of neutralizing serum antibodies and protection of the mice from lethal HSV-2 infection. Dose-titration studies show that low doses ($\leq 1$ µg) of either DNA construction induce protective immunity, and that a single immunization with the gD construction is also effective.

In a preferred embodiment of the present invention, full-length glycoprotein D (gD), and a truncated form of HSV-2 glycoprotein B (gB) are used in a low-dosage combination. Immune sera from DNA-injected animals had antibodies to both gD and gB, and virus neutralizing activity. When challenged by vaginal infection with HSV-2, the DNA-immunized animals were significantly protected from primary genital disease.

The present invention therefore relates to use of plasmid expression vectors encoding herpes simplex virus type 2 (HSV-2) proteins for their ability to immunize a host against a herpes infection. The protein may be expressed along or in combination with one or more additional proteins which will induce an immune response to HSV. It will be within the purview of the skilled artisan, after reviewing this specification, to choose one or more such proteins which may be a wild type, full-length version or a mutant version which retains immunogenicity and neutralizing activity. The skilled artisan will also be prompted as to the DNA vaccine dosage which will be useful in generating an immune response to HSV. For example, a preferred dosage rate for a combination polynucleotide vaccine expressing ΔgB and gD would be 2.0 ug gD and 0.6 ug ΔgB, respectively, in a guinea pig model. The skilled artisan will be able to manipulate these quantities and ratios to produce an optimal immune response in another host, such as a human. The skilled artisan will also be directed by the examples of this specification to utilize various HSV proteins and antigenic fragments thereof, such as amino or carboxy terminal trunctated forms, as well as mutated forms including but not limited to amino acid insertions, deletions and point mutations. These examples included DNA-mediated delivery of a gene fragment encoding glycoprotein B (gB) alone, glycoprotein C (gC) alone, glycoprotein D alone, a truncated version of gB, and combinational immunizations of DNA vaccines comprising gD and a truncated version of gB. By these teachings it will then be within the purview of the skilled artisan to utilize various other mutant versions (such as a truncated gD form or truncated gC form) alone or in combination with other disclosed DNA vaccine constructions to provide protection against HSV via delivery of a DNA vaccine.

In a preferred embodiment of the present invention, immunization with a plasmid expressing the amino-terminal 707 amino acids (aa) of gB is used to induce a humoral immune response detected by ELISA and virus neutralization. When challenged by vaginal infection, immunized animals are partially protected from genital herpes, exhibiting significantly reduced primary and subsequent recurrent disease.

In an especially preferred aspect of the present invention, a truncated gB plasmid is combined with a plasmid expressing full-length gD. The immunized host develops humoral responses to both proteins and are significantly protected from viral challenge.

Again, these nucleic acids are useful as vaccines for inducing immunity to HSV, which can prevent infection and/or ameliorate HSV-related disease.

The following examples are provided to illustrate the present invention without, however, limiting the same thereto.

EXAMPLE 1

Vectors for Vaccine Production

A) V1

The expression vector V1 was constructed from pCMVIE-AKI-DHFR [Y. Whang et al., *J. Virol.* 61, 1796 (1987)]. The AKI and DHFR genes were removed by cutting the vector with EcoR I and self-ligating. This vector does not contain intron A in the CMV promoter, so it was added as a PCR fragment that had a deleted internal Sac I site [at 1855 as numbered in B. S. Chapman et al., *Nuc. Acids Res.* 19, 3979 (1991)]. The template used for the PCR reactions was pCMVintA-Lux, made by ligating the Hind III and Nhe I fragment from pCMV6a120 [see B. S. Chapman et al., ibid.,] which includes hCMV-IE1 enhancer/promoter and intron A, into the Hind III and Xba I sites of pBL3 to generate pCMVIntBL. The 1881 base pair luciferase gene fragment (Hind III-Sma I Klenow filled-in) from RSV-Lux [J. R. de Wet et al., *Mol. Cell Biol.* 7, 725, 1987] was cloned into the Sal I site of pCMVIntBL, which was Klenow filled-in and phosphatase treated.

The primers that spanned intron A are:
5' primer, SEQ. ID:1:

5'-CTATATAAGCAGAG CTCGTTTAG-3';

The 3' primer, SEQ ID:2:
5'-GTAGCAAAGATCTAAGGACGGTGA CTGCAG-3'.

The primers used to remove the Sac I site are:
sense primer, SEQ ID:3:

5-GTATGTGTCTGAAAATGAGCGTGGAGATTGGGCTCGCAC-3' and the antisense primer, SEQ ID:4:
5'-GTGCGAGCCCAATCTCCACGCTCATTTTCAGACACA TAC-3'.

The PCR fragment was cut with Sac I and Bgl II and inserted into the vector which had been cut with the same enzymes.

B) V1J Expression Vector

The purpose in creating V1J was to remove the promoter and transcription termination elements from vector V1 in order to place them within a more defined context, create a more compact vector, and to improve plasmid purification yields.

V1J is derived from vectors V1 and pUC18, a commercially available plasmid. V1 was digested with SspI and EcoRI restriction enzymes producing two fragments of DNA. The smaller of these fragments, containing the CMVintA promoter and Bovine Growth Hormone (BGH) transcription termination elements which control the expression of heterologous genes, was purified from an agarose electrophoresis gel. The ends of this DNA fragment were then "blunted" using the T4 DNA polymerase enzyme in order to facilitate its ligation to another "blunt-ended" DNA fragment.

pUC18 was chosen to provide the "backbone" of the expression vector. It is known to produce high yields of plasmid, is well-characterized by sequence and function, and is of small size. The entire lac operon was removed from this vector by partial digestion with the HaeII restriction enzyme. The remaining plasmid was purified from an agarose electrophoresis gel, blunt-ended with the T4 DNA polymerase treated with calf intestinal alkaline phosphatase, and ligated to the CMVintA/BGH element described above. Plasmids exhibiting either of two possible orientations of the promoter elements within the pUC backbone were obtained. One of these plasmids gave much higher yields of DNA in *E. coli* and was designated V1J. This vector's structure was verified by sequence analysis of the junction regions and was subsequently demonstrated to give comparable or higher expression of heterologous genes compared with V1.

C) V1Jneo Expression Vector

It was necessary to remove the amp$^r$ gene used for antibiotic selection of bacteria harboring V1J because ampicillin may not be desirable in large-scale fermenters. The amp$^r$ gene from the pUC backbone of V1J was removed by digestion with SspI and Eam 1105I restriction enzymes. The remaining plasmid was purified by agarose gel electrophoresis, blunt-ended with T4 DNA polymerase, and then treated with calf intestinal alkaline phosphatase. The commercially available kan$^r$ gene, derived from transposon 903 and contained within the pUC4K plasmid, was excised using the PstI restriction enzyme, purified by agarose gel electrophoresis, and blunt-ended with T4 DNA polymerase. This fragment was ligated with the V1J backbone and plasmids with the kan$^r$ gene in either orientation were derived which were designated as V1Jneo #'s 1 and 3. Each of these plasmids was confirmed by restriction enzyme digestion analysis, DNA sequencing of the junction regions, and was shown to produce similar quantities of plasmid as V1J. Expression of heterologous gene products was also comparable to V1J for these V1Jneo vectors. V1Jneo#3, referred to as V1Jneo hereafter, was selected which contains the kan$^r$ gene in the same orientation as the amp$^r$ gene in V1J as the expression construct.

D) V1Jns Expression Vector

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

E) V1Jns-tPA

In order to provide an heterologous leader peptide sequence to secreted and/or membrane proteins, V1Jns was modified to include the human tissue-specific plasminogen activator (tPA) leader. Two synthetic complementary oligomers were annealed and then ligated into V1Jn which had been BglII digested. The sense and antisense oligomers were 5'-GATC ACC ATG GAT GCA ATG AAG AGA GGG CTC TGC TGT GTG CTG CTG CTG TGT GGA GCA GTC TTC GTT TCG CCC AGC GA-3', SEQ. ID:5:, and 5'-GAT CTC GCT GGG CGA AAC GAA GAC TGC TCC ACA CAG CAG CAG CAC ACA GCA GAG CCC TCT CTT CAT TGC ATC CAT GGT-3', SEQ. ID:6. The Kozak sequence is underlined in the sense oligomer. These oligomers have overhanging bases compatible for ligation to BglII-cleaved sequences. After ligation the upstream BglII site is destroyed while the downstream BglII is retained for subsequent ligations. Both the junction sites as well as the entire tPA leader sequence were verified by DNA sequencing. Additionally, in order to conform with the consensus optimized vector V1Jns (=V1Jneo with an SfiI site), an SfiI restriction site was placed at the KpnI site within the BGH terminator region of V1Jn-tPA by blunting the KpnI site with T4 DNA polymerase followed by ligation with an SfiI linker (catalogue #1138, New England Biolabs). This modification was verified by restriction digestion and agarose gel electrophoresis.

F) pGEM-3-X-IRES-B7

(where X=any antigenic gene) As an example of a dicistronic vaccine construct which provides coordinate expression of a gene encoding an immunogen and a gene encoding an immuno-stimulatory protein, the murine B7 gene was PCR amplified from the B lymphoma cell line CH1 (obtained from the ATCC). B7 is a member of a family of proteins which provide essential costimulation T cell activation by antigen in the context of major histocompatibility complexes I and II. CH1 cells provide a good source of B7 mRNA because they have the phenotype of being constitutively activated and B7 is expressed primarily by activated antigen presenting cells such as B cells and macrophages. These cells were further stimulated in vitro using cAMP or IL-4 and mRNA prepared using standard guanidinium thiocyanate procedures. cDNA synthesis was performed using this mRNA using the GeneAmp RNA PCR kit (Perkin-Elmner Cetus) and a priming oligomer (5'-GTA CCT CAT GAG CCA CAT AAT ACC ATG-3', SEQ. ID:7:) specific for B7 located downstream of the B7 translational open reading frame. B7 was amplified by PCR using the following sense and antisense PCR oligomers: 5'-GGT ACA AGA TCT ACC ATG GCT TGC AAT TGT CAG TTG ATG C-3', SEQ. ID:8:, and 5'-CCA CAT AGA TCT CCA TGG GAA CTA AAG GAA GAC GGT CTG TTC-3', SEQ. ID:9:, respectively. These oligomers provide BglII restriction enzyme sites at the ends of the insert as well as a Kozak translation initiation sequence containing an NcoI restriction site and an additional NcoI site located immediately prior to the 3'-terminal BglII site. NcoI digestion yielded a fragment suitable for cloning into pGEM-3-IRES which had been digested with NcoI. The resulting vector, pGEM-3-IRES-B7, contains an IRES-B7 cassette which can easily be transferred to V1Jns-X, where X represents an antigen-encoding gene.

G) pGEM-3-X-IRES-GM-CSF (where X=any antigenic gene) This vector contains a cassette analogous to that described in item C above except that the gene for the immunostimulatory cytokine, GM-CSF, is used rather than B7. GM-CSF is a macrophage differentiation and stimulation cytokine which has been shown to elicit potent anti-tumor T cell activities in vivo [G. Dranoff et al., Proc. Natl. Acad. Sci. USA, 90, 3539 (1993).

H) pGEM-3-X-IRES-IL-12

(where X=any antigenic gene) This vector contains a cassette analogous to that described in item C above except that the gene for the immunostimulatory cytokine, IL-12, is used rather than B7. IL-12 has been demonstrated to have an influential role in shifting immune responses towards cellular, T cell-dominated pathways as opposed to humoral responses [L. Alfonso et al., Science, 263, 235, 1994].

EXAMPLE 2

Vector V1R Preparation

In an effort to continue to optimize the basic vaccination vector, a derivative of V1Jns, designated V1R, was prepared. The purpose for this vector construction was to obtain a minimum-sized vaccine vector without unneeded DNA sequences, which still retained the overall optimized heterologous gene expression characteristics and high plasmid yields that V1J and V1Jns afford. It was determined from the literature as well as by experiment that (1) regions within the pUC backbone comprising the E. coli origin of replication could be removed without affecting plasmid yield from bacteria; (2) the 3'-region of the $kan^r$ gene following the kanamycin open reading frame could be removed if a bacterial terminator was inserted in its place; and, (3) ~300 bp from the 3'-half of the BGH terminator could be removed without affecting its regulatory function (following the original KpnI restriction enzyme site within the BGH element).

V1R was constructed by using PCR to synthesize three segments of DNA from V1Jns representing the CMVintA promoter/BGH terminator, origin of replication, and kanamycin resistance elements, respectively. Restriction enzymes unique for each segment were added to each segment end using the PCR oligomers: SspI and XhoI for CMVintA/BGH; EcoRV and BamHI for the $kan^r$ gene; and, BclI and SalI for the $ori^r$. These enzyme sites were chosen because they allow directional ligation of each of the PCR-derived DNA segments with subsequent loss of each site: EcoRV and SspI leave blunt-ended DNAs which are compatible for ligation while BamHI and BclI leave complementary overhangs as do SalI and XhoI. After obtaining these segments by PCR each segment was digested with the appropriate restriction enzymes indicated above and then ligated together in a single reaction mixture containing all three DNA segments. The 5'-end of the $ori^r$ was designed to include the T2 rho independent terminator sequence that is normally found in this region so that it could provide termination information for the kanamycin resistance gene. The ligated product was confirmed by restriction enzyme digestion (>8 enzymes) as well as by DNA sequencing of the ligation junctions. DNA plasmid yields and heterologous expression using viral genes within V1R appear similar to V1Jns. The net reduction in vector size achieved was 1346 bp (V1Jns=4.86 kb; V1R=3.52 kb).

PCR oligomer sequences used to synthesize V1R (restriction enzyme sites are underlined and identified in brackets following sequence):

(1) 5'-GGT ACA AAT ATT GG CTA TTG GCC ATT GCA TAC G-3' [SspI], SEQ.ID:10:, (2) 5'-CCA CAT CTC GAG GAA CCG GGT CAA TTC TTC AGC ACC-3' [XhoI], SEQ.ID:11:

(for CMVintA/BGH segment)

(3) 5'-GGT ACA GAT ATC GGA AAG CCA CGT TGT GTC TCA AAA TC-3'[EcoRV], SEQ.ID:12:

(4) 5'-CCA CAT GGA TCC G TAA TGC TCT GCC AGT GTT ACA ACC-3' [BamHI], SEQ.ID:13:

(for kanamycin resistance gene segment)

(5) 5'-GGT ACA TGA TCA CGT AGA AAA GAT CAA AGG ATC TTC TTG-3'[BclI], SEQ.ID:14:, (6) 5'-CCA CAT GTC GAC CC GTA AAA AGG CCG CGT TGC TGG-3' [SalI], SEQ ID:15:

(for *E. coli* origin of replication)

EXAMPLE 3
Cells, Viruses and Cell Culture

VERO, BHK-21, RD cells and HSV-2 strain MS were obtained from the ATCC. Virus was routinely prepared by infection of nearly confluent VERO or BHK cells with a multiplicity of infection (m.o.i.) of 0.1 at 37° C. in a small volume of medium without fetal bovine serum (FBS). After one hour, virus inoculum was removed and cultures were re-fed with high glucose DMEM supplemented with 2% heat-inactivated FBS, 2 mM L-glutamine, 25 mM HEPES, 50 U/ml penicillin and 50 µg/ml streptomycin. Incubation was continued until cytopatic effect was extensive: usually 24 to 48 hours. Cell associated virus was collected by centrifugation at 1800×g 10 minutes 4° C. Supernatant virus was clarified by centrifugation at 640×g for 10 minutes 4° C.

EXAMPLE 4
Cloning and DNA Preparation

HSV-2 (Curtis) DNA for use as PCR template was prepared from nucleocapsids isolated from infected VERO cells. (Denniston, K. J. et al., 1981, Gene, 15, pp.365–378) Synthetic oligomers corresponding to 5' and 3' end flanking sequences for the HSV2 gB, gC, gD, or ICP27 genes, containing Bgl II restriction recognition sites (Midland Certified Reagent Company; Midland, Tex.) were used at 20 pmoles each. A 1.1 kb fragment encoding the gD gene was amplified by PCR (Perkin Elmer Cetus, La Jolla) according to the manufacturer's specifications except that a deaza dGTP:dGTP ratio of 1:4 was used in place of dGTP and the buffer was supplemented to 3 mM Mg Cl$_2$. HSV-2 genomic DNA template was used at 100 ng/100 µl reaction. The PCR amplified fragments were restricted with Bgl II and ligated to the Bgl II digested, dephosphorylated vector V1J (Montgomery, D. L. et al., supra). *E. coli* DH5α (BRL-Gibco, Gaithersburg, Md.) was transformed according to the manufacturer's specifications. Ampicillin resistant colonies were screened by hybridization with the $^{32}$P labeled 3' PCR primer. Candidate plasmids were characterized by restriction mapping and sequencing of the vector-insert junctions using the Sequenase DNA Sequencing Kit, version 2.0 (United States Biochemical). In a similar manner, a 2.7 Kb fragment encoding the gB gene; a 1.5 Kb fragment encoding the gC gene; and a 1.6 Kb fragment encoding the ICP27 gene were also PCR amplified. Independently derived isolates were identified and characterized for the presence of the correct DNA construct containing either the gB, gC, gD, or ICP27 gene.

Large scale DNA preparation was essentially as described (Montgomery, D. L. et al., supra) except that 800 ml cultures were grown for 24 to 48 hours and for some experiments DNA was purified by a single CsCl-EtBr isopyncnic density centifugation.

The plasmid constructions were characterized by restriction mapping and sequence analysis of the vector-insert junctions. Results were consistent with published HSV-2 strain G (Lasky, L. A. et al., 1984, DNA, 3, pp.23–29) sequence data and showed that initiation and termination codons were intact for each construct.

EXAMPLE 5
Expression of HSV-2gB gC, gD and ICP27 Proteins from V1J Plasmids

Rhabdomyosarcoma cells (ATCC CCL136) were planted one day before use at a density of 1.2×10$^6$ cells per 9.5 cm$^2$ well in six-well tissue culture clusters in high glucose DMEM supplemented with 10% heat-inactivated fetal calf serum, 2 mM L-glutamine, 25 mM HEPES, 50 U/ml penicillin and 50 µg/ml streptomycin. (All from BRL-Gibco) Phenol: chloroform extracted cesium chloride purified plasmid DNA was precipitated with calcium phosphate using Pharmacia CellPhect reagents according to the kit instructions except that 5–15 µg is used for each 9.5 cm$^2$ well of RD cells. Cultures were glycerol shocked six hours post addition of calcium phosphate-DNA precipate; after refeeding, cultures were incubated for two days prior to harvest.

Lysates of transfected cultures were prepared in 1× RIPA (0.5% SDS, 1.0% TRITON X-100, 1% sodium deoxycholate, 1 mM EDTA, 150 mM NaCl, 25 mM TRIS-HCl pH 7.4) supplemented with 1 µM leupeptin, 1 µM pepstatin, 300 nM aprotinin, and 10 µM TLCK, and sonicated briefly to reduce viscosity. Lysates were resolved by electrophoresis on 10% Tricine gels (Novex) and then transferred to nitrocellulose membranes. Immunoblots were processed with HSV-2 convalescent mouse sera and developed with the ECL detection kit (Amersham).

Expression of HSV gD from V1J:gD was demonstrated by transient transfection of RD cells. Lysates of V1J:gD-transfected or mock transfected cells were fractionated by SDS PAGE and analyzed by immunoblotting. FIG. 1A shows that V1J:gD transfected RD cells express an immunoreactive protein with an apparent molecular weight of approximately 55 K. Lysates from HSV-2 (Curtis), HSV-2 (186), or mock-infected Vero cells are included for comparison. The identical migrations of cloned gD and the authentic protein from infected cells indicates that the protein is full-length, and is processed and glycosylated similarly to that of gD in HSV-infected cells. Indirect immunofluorescence of fixed V1J:gD transfected cells showed a diffuse cytoplasmic signal.

Expression of HSV gB from V1JNS:gB was demonstrated by transient transfection of RD cells. Lysates of V1JNS:gB-transfected or mock transfected cells were fractionated by SDS PAGE and analyzed by immunoblotting. FIG. 1B shows that V1JNS:gB transfected RD cells express an immunoreactive protein with an apparent molecular weight of approximately 140 k. Lysates from HSV-2 (Curtis), HSV-2 (186), or mock infected Vero cells are included for comparison. The similar migrations of cloned gB and the authentic protein from infected cells shows that the protein is full-length. Indirect immunofluorescence of fixed V1JNS:gB transfected cells showed a membrane-associated punctate signal.

Expression of HSV gC from V1J:gC was demonstrated by transient transfection of RD cells. Indirect immunofluorescence of fixed V1J:gC transfected cells showed primarily a diffuse cytoplasmic signal.

Expression of ICP27 was demonstrated by transient transfection of RD cells, followed by Western blot analysis. A mouse monoclonal antibody specific for ICP27 detected a protein of about 60 k Da, which is consistent with the major immunoreactive protein in HSV 2 infected cells (FIG. 1C).

EXAMPLE 6

Immunization with PNV and Detection of Anti-HSV Antibodies

Five- to six-week-old female BALB/c mice were anesthetized by intraperitoneal (i.p.) injection of a mixture of 5 mg ketamine HCl (Aveco, Fort Dodge, Iowa) and 0.5 mg xylazine (Mobley Corp., Shawnee, Kans.) in saline. The hind legs were shaved with electric clippers and washed with 70% ethanol. Animals were injected with a total of 100 µl of DNA suspended in saline: 50 µl each leg.

The ability of V1J:gD DNA to elicit an immune response to HSV gD was first examined in a titration experiment. Groups of ten mice received i.m. injections of DNA in a dose range from 200 µg to 0.78 µg (8 two-fold dilutions) or were sham immunized with saline. Sera, obtained four and six weeks post immunization, were analyzed by ELISA. For the ELISA, HSV-2 glycoprotein was diluted to 5 µg/ml in 50 mM carbonate buffer pH 9.5. Nunc Maxi-sorb flat bottom 96-well plates were coated at 4° C., overnight with 100 µl per well of HSV glycoproteins. Plates were washed four times with PBS pH 7.2 and nonspecific reactivity was reduced with blocking and dilution buffer, 20 mM TRIS-HCl pH 7.5, 137 mM NaCl, 2.7 mM KCl, 0.5% gelatin, 0.05% Tween 20 for one hour at room temperature. Serial dilutions of mouse sera were added, and plates were incubated one hour at room temperature. Plates were washed four times with PBS and once with distilled water prior to the addition of alkaline phosphatase-labeled goat anti mouse IgG (Boehringer Mannheim, Indianapolis, Ind.) and incubated for one hour at room temperature. Excess secondary antibody was removed with four PBS washes followed by one distilled water wash. The ELISA was developed with the addition of 100 µl per well of 1 mg/ml p-nitrophenylphosphate in 10% diethanolamine pH 9.8 100 µg/ml MgCl.6 H$_2$O at 37° C. Absorbance was read at 405 nm and serum dilutions were scored as positive if the OD$_{405}$ was greater than the mean plus three standard deviations of the same dilution of the saline control sera. By four weeks the majority of animals receiving ≧6.25 µg of DNA were seropositive. At doses lower than 6.25 µg, fewer animals had seroconverted, however even at the lowest dose some animals were ELISA positive. None of the saline injected control animals were positive. At six weeks a majority of the animals had become seropositive.

At seven weeks, the animals were re-immunized with the same doses of DNA (or saline) used in the initial injections. Sera were obtained at ten weeks (three weeks after the second injection) and endpoint titers were determined by ELISA. The results are summarized in Table 1. By ten weeks, 93% of the DNA injected mice were seropositive. Even at the 0.78 µg dose, eight of the nine animals were positive.

TABLE 1

Seroconversion of mice immunized with V1J:gD DNA[a]

| DNA dose (µg) | no. seropositive/no. immunized | ELISA GMT[b] |
|---|---|---|
| 200 | 9/9 | 31,808 |
| 100 | 10/10 | 44,904 |
| 50 | 9/10 | 8,027 |
| 25 | 8/8 | 13,512 |
| 12.5 | 10/10 | 14,199 |
| 6.25 | 10/10 | 16,016 |
| 3.13 | 10/10 | 9,054 |
| 1.56 | 7/10 | 360 |

TABLE 1-continued

Seroconversion of mice immunized with V1J:gD DNA[a]

| DNA dose (µg) | no. seropositive/no. immunized | ELISA GMT[b] |
|---|---|---|
| 0.78 | 8/9 | 4,641 |
| saline | 0/10 | 10 |

[a]Mice were immunized at weeks 0 and 7 with the indicated amount of DNA. Sera were obtained at 10 weeks and assayed as described herein.
[b]For purposes of calculating the GMT, sera negative at the lowest dilution tested (1:30), were assigned a value equal to one dilution less, i.e. 1:10.

Figure 2A:
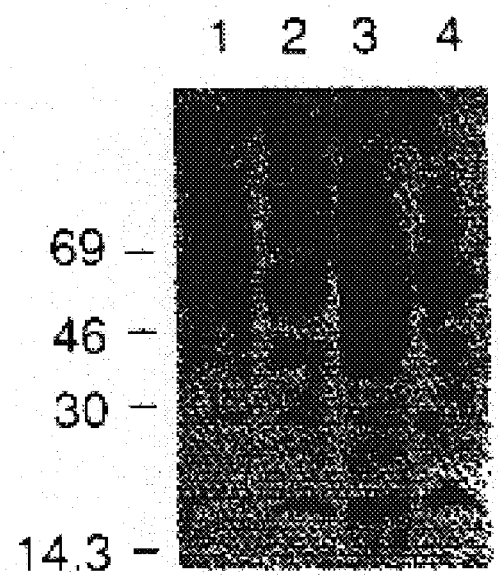
FIG. 2. Panels A, B, and C
Western blot analysis using sera from HSV PNV-immunized (B-6.25 ug dose of V1J:gD, C-50 ug dose of V1J:gD) and sham immunized (A) animals is shown on lysates of BHK cells infected with:
1. HSV-1 KOS;
2. HSV-2 186;
3. HSV-2 Curtis;
4. mock infected.

Panel D. Western blot analysis using sera from HSV PNV gB immunized animals is shown.

To confirm that the ELISA reactivity was due to anti-gD antibodies, several high ELISA titer sera were characterized by their reactivity with immunoblots of HSV or mock-infected cell lysates. FIG. 2A illustrates that sera from V1J:gD immunized mice react specifically with a single HSV encoded protein with an electrophoretic mobility consistent with that of HSV gD. Taken together, these data show that i.m. injection of mice with V1J:gD DNA results in the expression of gD epitopes and the development of an immune response to gD protein.

To extend these results and to establish the minimal effective PNV dose, V1J:gD was titrated further in an experiment where animals were immunized only once. Groups of mice were injected with V1J:gD DNA ranging from 5 ng to 50 µg. Sera collected at four, seven, and ten weeks post immunization were assayed by ELISA; the data are summarized in FIG. 3.

This titration reveals a threshold of response of about 0.5 µg DNA. While a few animals receiving lower amounts of DNA were seropositive by ELISA, the positive response was transient and occurred only at the lowest serum dilution. At DNA doses of ≧1.67 μg, more than 90% of animals seroconverted by four weeks and remained positive at seven and ten weeks.

Increases in antibody titers of individual animals with time are reflected by increases in the group GMTs seen in FIG. 3. At doses ≧0.5 μg, the GMT rises sharply between four and seven weeks. Between seven and ten weeks, the titers increase or remain constant in all but one case. The ten-week ELISA titers of animals receiving ≧0.5 μg are similar to those attained in the previous experiment where a second DNA immunization was given. The amounts of PNV required to provoke an immune response was as much as 100-fold less than published reports using similar vectors. (Robinson et al., 1993, Vaccine, 11, pp.957–960; and Fynan et al., 1993, Proc.Natl.Acad.Sci. USA, 90, pp.1 1478–11482)

In order to establish a standardized protocol, the effectiveness of one- and two-dose immunization was compared. In the two-dose experiment, we found no significant differences in protection at the highest (200 μg) dose and the lowest (0.78 μg) dose. When the titration was extended in the single-dose experiment, a dose response for ELISA GMT was observed, showing efficiency of seroconversion and protection. The threshold for these responses was about 0.5 μg. However, seroconversion does occur with as little as 50 ng of DNA. In general, titers continued to rise through ten weeks after a single injection and in the two-dose experiment there was no obvious boost in titers after the second injection. Finally, at 50 μg of DNA, the only dose common to both experiments, there were no significant differences between one and two doses.

Similar analyses as set forth above were done for the PNV constructions containing the HSV genes gB and gC. Mice (10 mice per group) were immunized as described above with DNA containing the HSV gB gene or DNA containing the HSV gC gene. Serum was collected and analyzed for the presence of anti-gB or anti-gC antibodies in the ELISA described above. The ELISA data for gB antibodies are shown in Table 2, and demonstrates that mice immunized with V1JNS:gB were seropositive for anti-gB antibodies.

TABLE 2

10 WEEK SERA ELISA gB

| Treatment | weeks | GMT | SEM (range) |
|---|---|---|---|
| saline | 0 | 3 | 3–3 |
| 1 ug | 0 | 3 | 3–3 |
| 1 ug | 0, 7 | 3 | 3–3 |
| 3 ug | 0 | 6 | 4–10 |
| 3 ug | 0, 7 | 24 | 8–68 |
| 10 ug | 0 | 48 | 13–170 |
| 10 ug | 0, 7 | 150 | 38–595 |
| 30 ug | 0 | 300 | 87–1034 |
| 30 ug | 0, 7 | 39 | 10–150 |
| 100 ug | 0 | 378 | 69–2062 |
| 100 ug | 0, 7 | 7536 | 1893–30,000 |

The ELISA data for gC antibodies are shown in Table 3, and demonstrates that mice (five mice per group) immunized with V1J:gC were seropositive for anti-gC antibodies.

TABLE 3

10 WEEK SERA ELISA gC

| Treatment | weeks | GMT | SEM (range) |
|---|---|---|---|
| saline | 0 | 10 | 10–10 |
| 10 ug | 0, 7 | 4642 | 2154–10,000 |
| 100 ug | 0, 7 | 3162 | 1440–6943 |

Figure 2B:
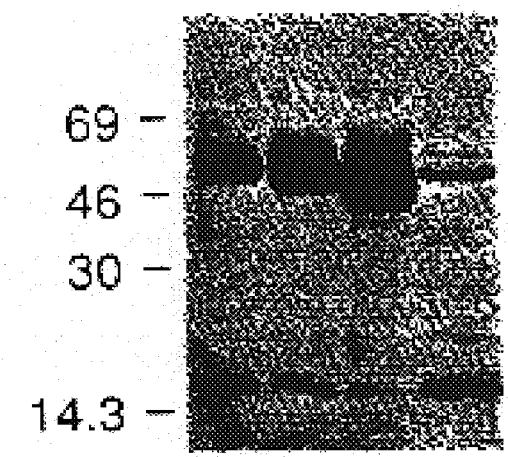
Figure 2C:
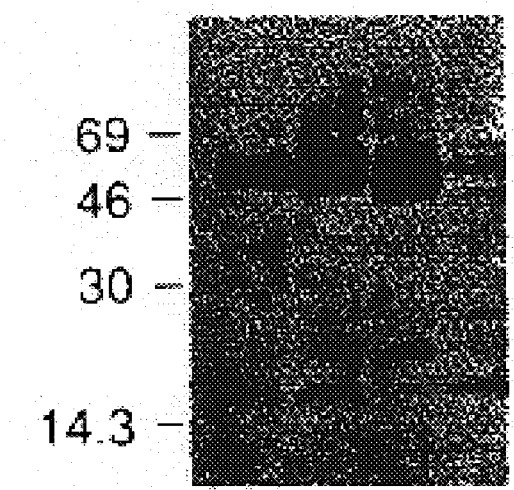
Figure 2D:
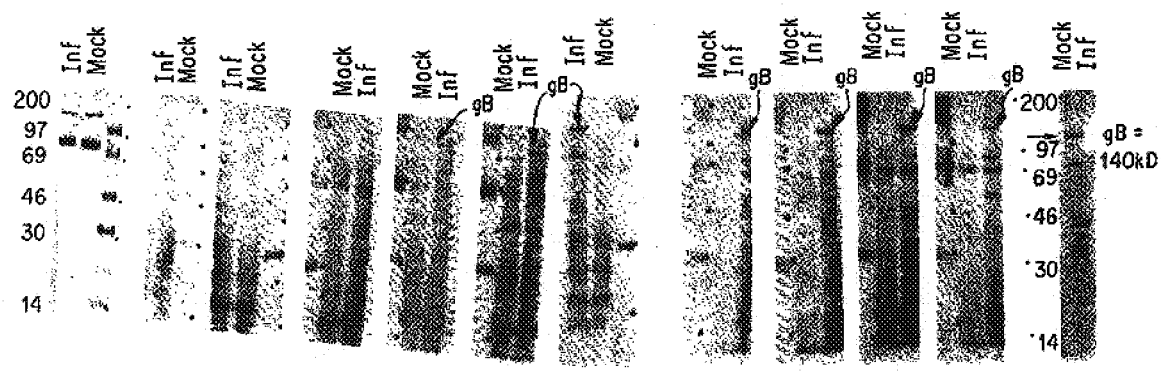

To confirm that the ELISA reactivity for gB was due to anti-gB antibodies, several high ELISA titer sera were characterized by their reactivity with immunoblots of HSV or mock infected cell lysates. FIG. 2B illustrates that sera from V1JNS:gB immunized mice reacts specifically with a single HSV encoded protein with an electrophoretic mobility consistent with that of HSV gB. Taken together, these data show that i.m. injection of mice with HSV PNV results in the expression of HSV epitopes and the development of an immune response to those HSV proteins.

EXAMPLE 7
HSV Neutralization

Mouse sera were heat-inactivated at 56° C. 30 minutes prior to serial dilution in DMEM, 2% heat inactivated FBS and then 50 µl of each dilution was delivered to duplicate wells in a sterile polypropylene 96 deep well plate (Marsh Biomedical, Rochester, N.Y.). HSV-1 or HSV-2 stocks were diluted to 4,000 pfu/ml, 50 µl of virus were then added to each sample well and the plate was incubated overnight at 4° C. Guinea pig complement (Cappel) was diluted 1:4 in DMEM, 2% heat inactivated FBS and 50 µl were added to each sample well. After a one hour incubation at 37° C., 100 µl of serum free medium was added to each well and each reaction mixture was used to infect confluent VERO cells in 12-well cluster plates. (Costar) Neutralized virus samples were adsorbed for one hour at 37° C. Inocula were gently aspirated and monolayers were overlaid with 1 ml 0.5% carboxymethylcellulose 1× MEM 5% heat inactivated FBS 10 mM l-glutamine, 25U/ml penicillin, 25 µg/ml streptomycin, 12.5 mM HEPES. Plates were incubated at 37° C. for 48 hours. Overlays were removed and cell monolayers were stained with 1% basic fuchsin, 50% methanol 10% phenol. Plaques were counted and the neutralization titer was determined as the serum dilution which yielded a 50% reduction in plaque number when compared to sera from sham-immunized mice.

To determine whether the anti-gD antibodies might be biologically active, selected high-titer ten-week sera from mice immunized at zero and seven weeks were assayed for HSV-2 neutralizing activity. The results of plaque reduction assays are in Table 4. Sera from V1J:gD immunized mice neutralized not only HSV-2 (Curtis) but also HSV-2 (186). Furthermore, at least some of the sera contain type common neutralizing antibodies as shown by their neutralization of HSV-1 (KOS) infectivity. Although the neutralizing titers were low in some cases, these results encouraged us to see if these anti-gD antibodies could protect the animals against a lethal HSV challenge.

Ten week sera from all animals immunized with ≧0.5 µg V1J:gD in the single-dose experiment were also tested in an HSV-2 plaque reduction assay. Twenty-nine of the forty-nine sera assayed were positive: >50% plaque reduction at a 1:10 dilution. At the 16.7 and 50 µg dose level, nine of ten sera from each group were neutralization positive.

TABLE 4

| | HSV-2 Curtis neutralization | | | | |
|---|---|---|---|---|---|
| | (serum dilution) | | | | |
| animal no. | 1:10 | 1:100 | 1:1000 | DNA dose (µg) | ELISA titer |
| 4353 a | + | + | − | 3.13 | ≧33,333 |
| 4354 | + | + | − | 3.13 | 33,333 |
| 4362 | + | + | − | 6.25 | ≧33,333 |
| 4363 b | + | − | − | 6.25 | ≧33,333 |
| 4371 | + | + | − | 12.5 | ≧33,333 |
| 4391 | + | + | + | 50 | 1000 |
| 4392 a | + | + | + | 50 | 10,000 |
| 4393 | − | − | − | 50 | 333 |
| 4395 | − | − | − | 50 | ≦100 |
| 4396 b | + | + | − | 50 | ≧33,333 |
| 4397 | + | − | − | 50 | ≧33,333 |
| 4398 | + | + | + | 50 | ≧33,333 |
| 4399 | + | + | + | 50 | ≧33,333 |
| 4400 | + | + | − | 50 | 3,333 |
| 4405 b | + | + | + | 100 | 100,000 | a-neutralizes HSV-1 KOS at 1:100.
b-neutralized HSV-2 186 at 1:100.

EXAMPLE 8
HSV Challenge

Stocks of challenge virus were prepared by infection of confluent VERO monolayers with HSV-2 Curtis as described above. Clarified supernatant virus was titered on VERO cells and aliquots were stored at −70° C. Animals were infected by i.p. injection with 0.25 ml of virus stock and then observed for three weeks. Survival data were analyzed using the log-rank test (McDermott et al., 1989, Virology, 169, pp.244–247) in the SAS® procedure LIFETEST. Differences in probability ≦0.001 were judged highly significant.

Figure 4:
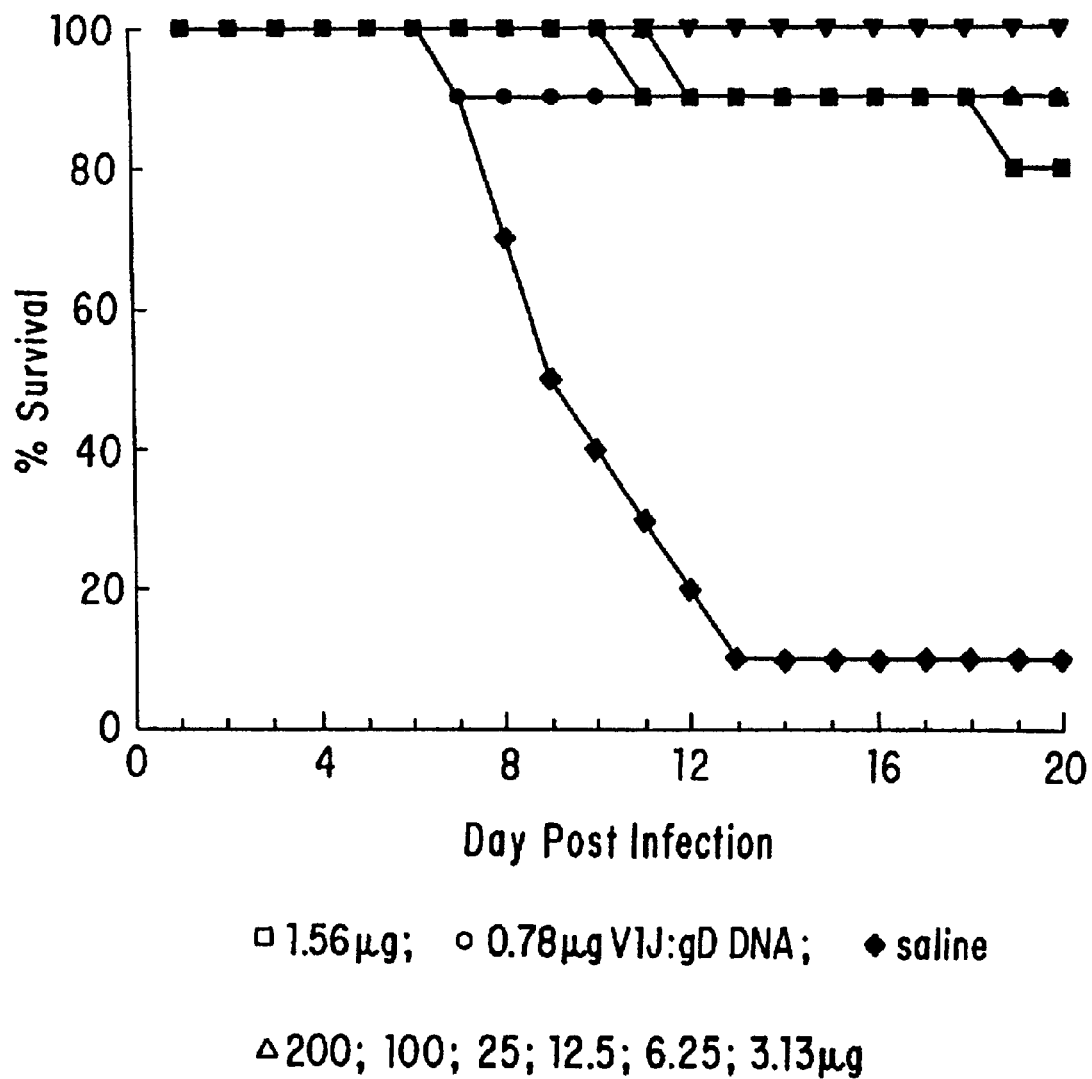
FIG. 4. Survival of HSV-2 challenged animals following two injections with V1J:gD at 200 ug; 100 ug; 50 ug; 25 ug; 12.5 ug; 6.25 ug; 3.13 ug; 1.56 ug; 0.78 ug; or saline only. Since all animals in the 200 ug; 100 ug; 25 ug; 12.5 ug; 6.25 ug; and 3.13 ug groups survived, they are all represented with a single symbol.

Eleven weeks after the initial DNA injection, mice immunized with two doses of V1J:gD were challenged by i.p. injection of $10^{5.7}$ p.f.u. of HSV-2 (Curtis) and observed for 21 days. Survival data are in FIG. 4. It is readily apparent that animals immunized with as little 0.78 µg of V1J:gD were significantly protected from lethal infection. Of the three immunized animals that died, two were seronegative by ELISA at ten weeks. A few of the surviving animals did show signs of transient illness including failure to groom, failure to thrive, or a hunched posture. While the level of protection from death achieved at every dose of DNA was significant (p<0.01), these symptoms suggest some breakthrough infection occurred. Analysis of sera obtained from convalescent animals were characterized by their reaction in immunoblots of HSV-2 infected Vero cell lysates. In some cases, a serum recognized only gD and in others, the serum reacted with many HSV proteins. These results are consistent with at least some of the mice having experienced HSV infection.

Figure 3:
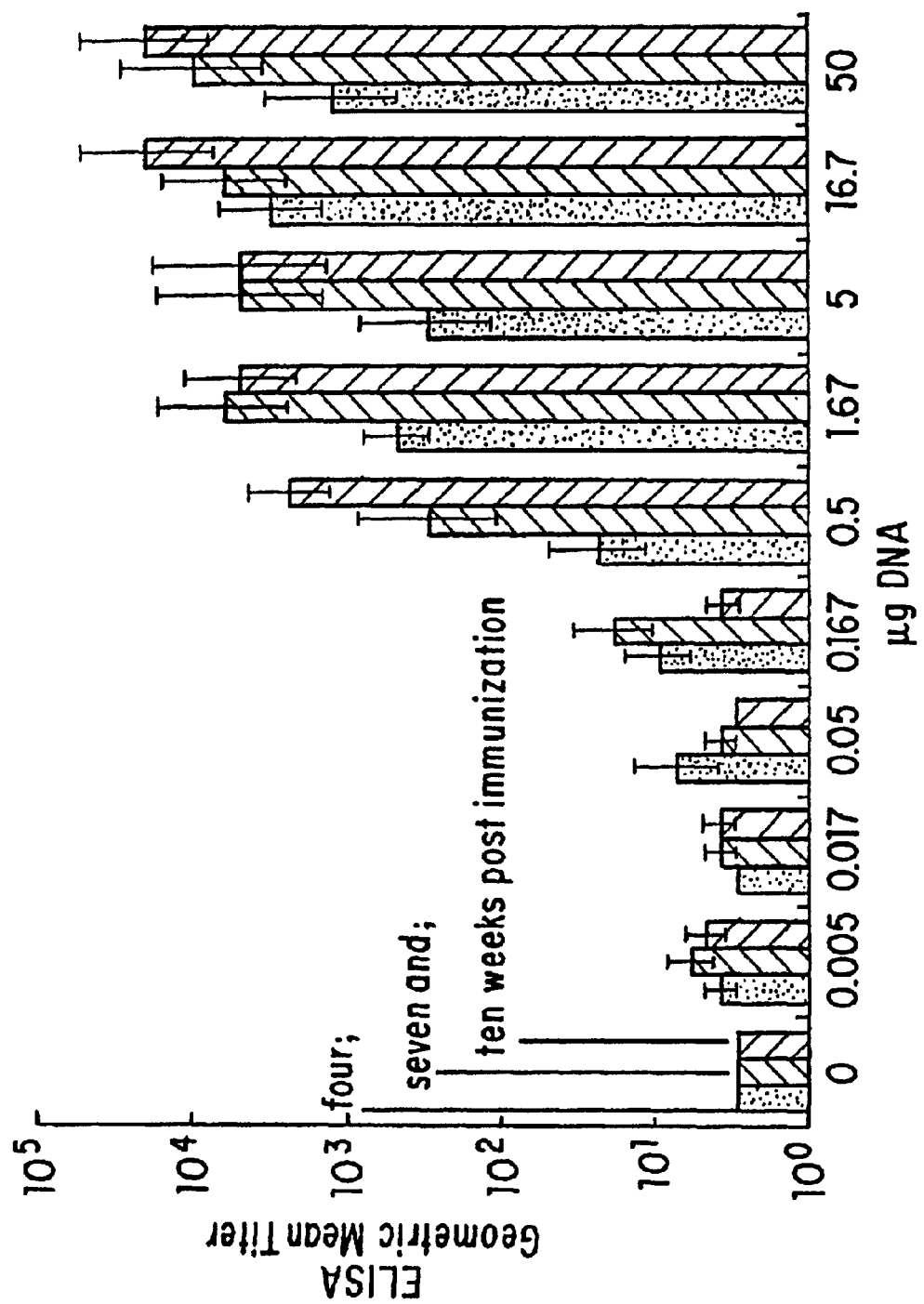
FIG. 3. ELISA generated group GMT data is shown for HSV PNV-immunized animals receiving a single injection of vaccine; sera were obtained at 4, 7 and 10 weeks post-immunization.
Figure 5:
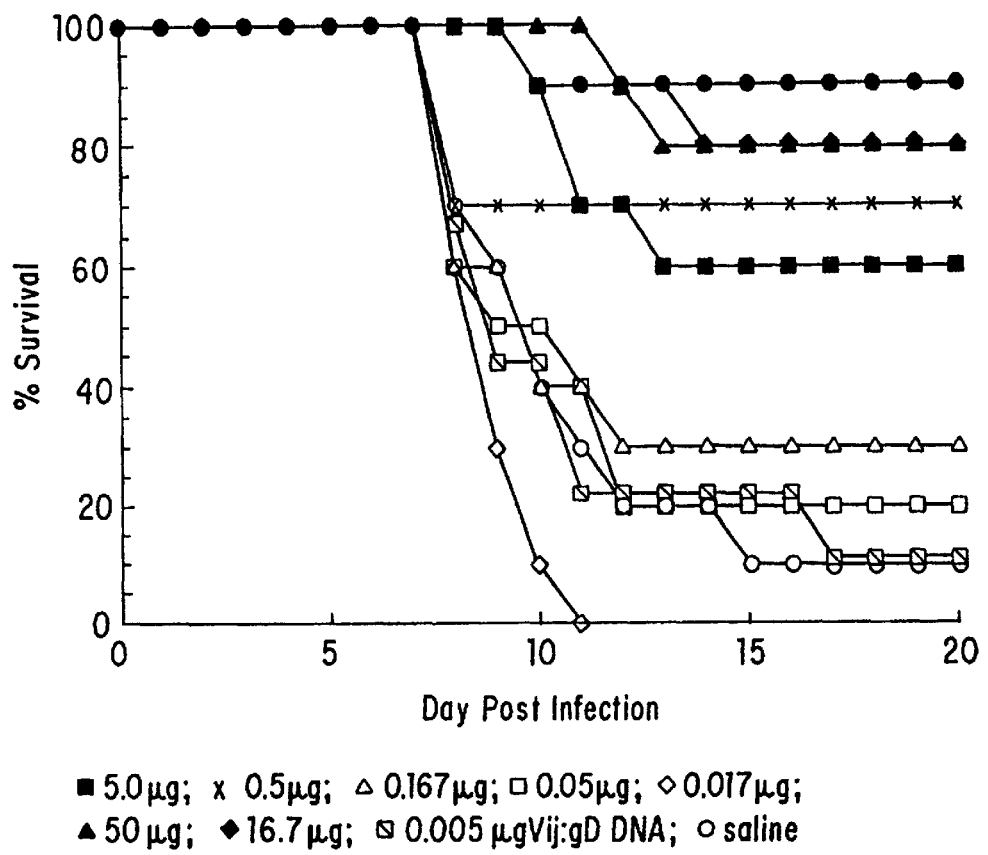

Animals immunized with a single DNA injection were challenged as described above. Survival data are presented in FIG. 5. Statistically significant (p<0.001) protection against death was obtained in groups of animals receiving ≧1.67 µg V1J:gD. This survival dose response is similar to that seen for ELISA titer (FIG. 3). As was seen in the two-dose experiment, a few surviving animals displayed transient signs of illness during the observation period. Surviving animals immunized with higher doses of DNA (16.7 and 50 µg) remained sleek and healthy-looking throughout the observation period.

Figure 6:
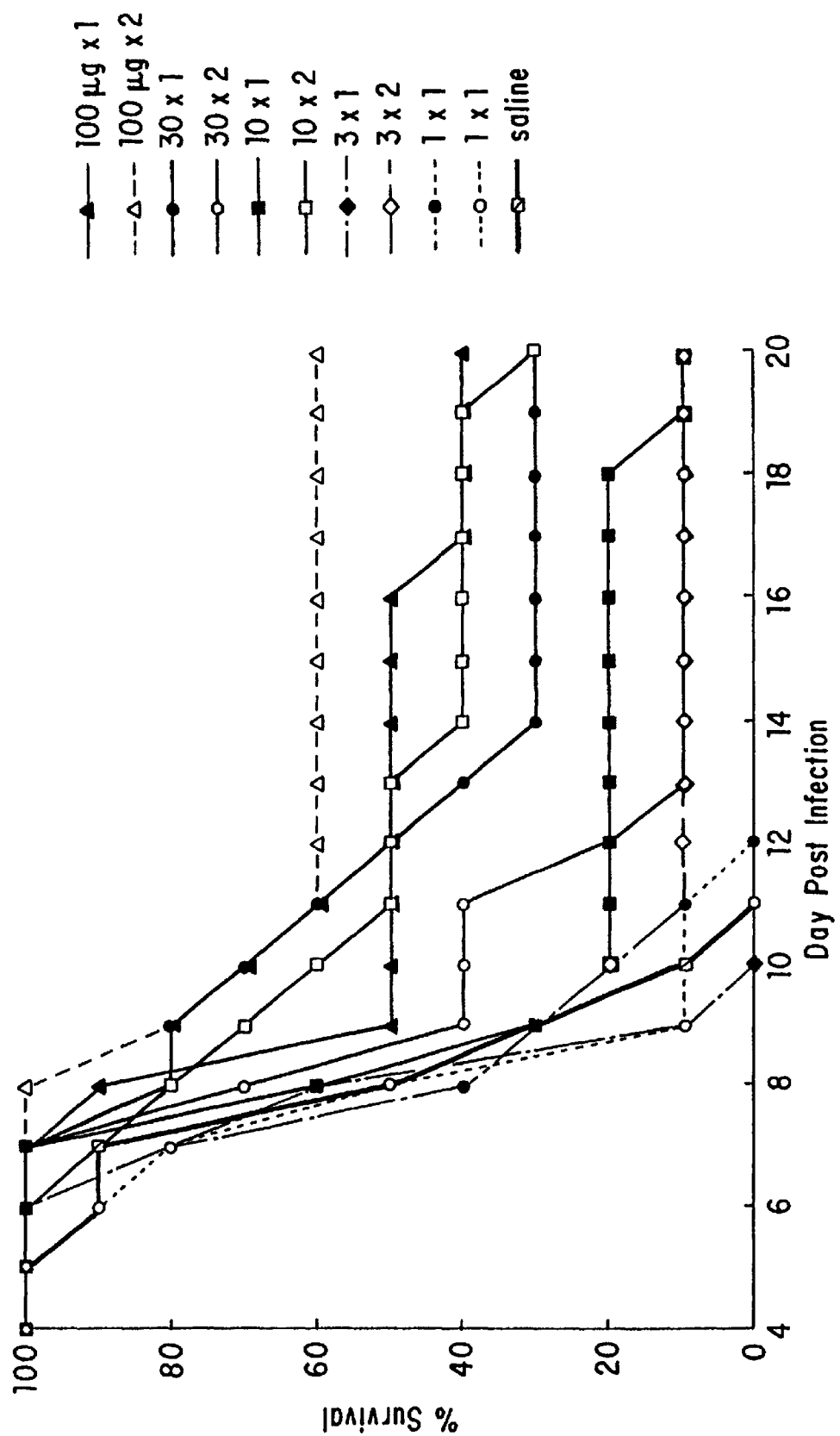
Figure 7:
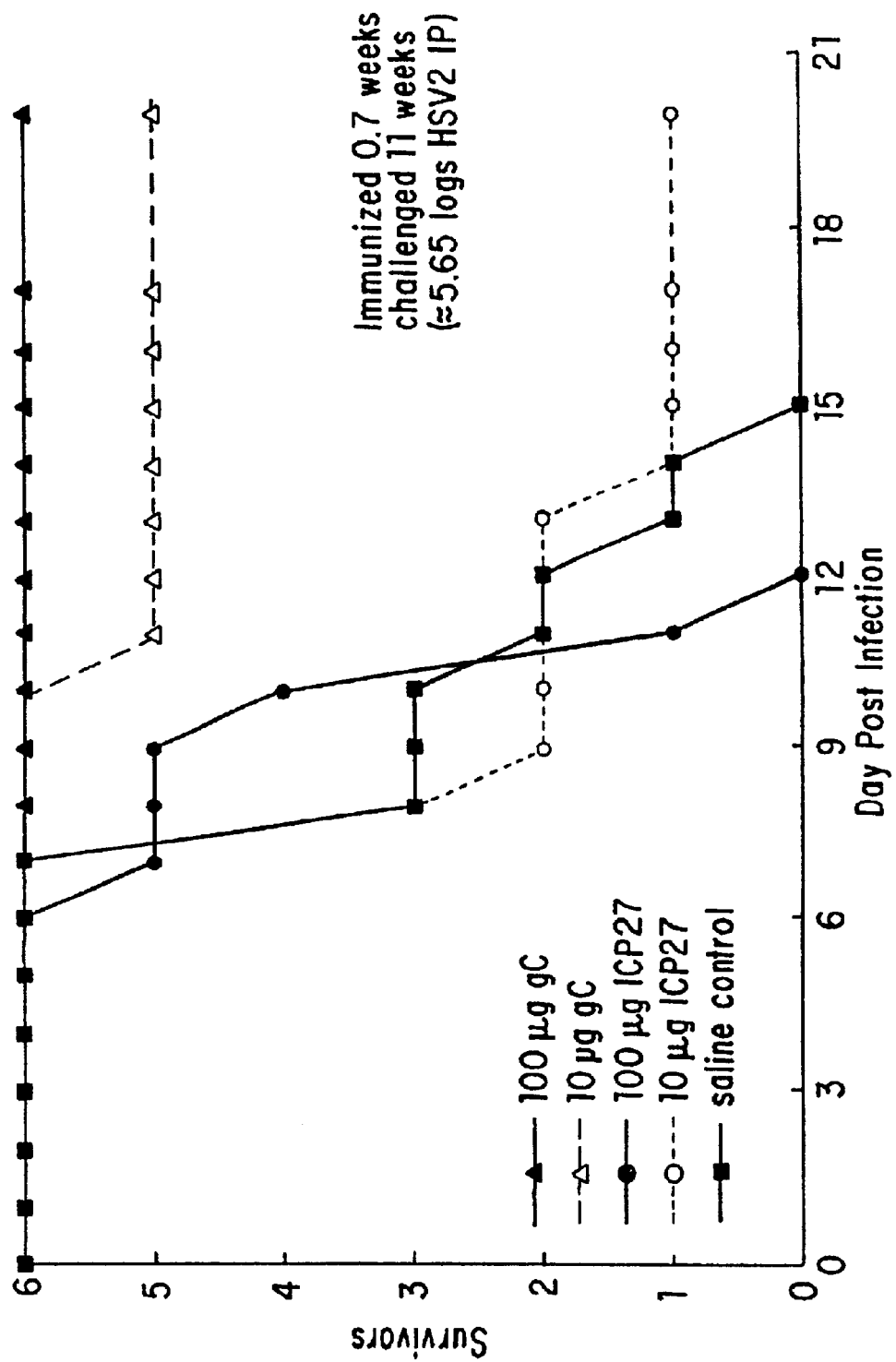

Animals immunized with PNV constructs containing HSV gB or gC genes were also challenged with a lethal dose of HSV as described above for gD. Survival data for animals immunized with V1JNS:gB are shown in FIG. 6, and survival data for animals immunized with V1J:gC are shown in FIG. 7 demonstrating that protection from death was obtained.

These results demonstrate the potential for direct DNA immunization in the prevention of HSV infection. Using glycoprotein gD as a model, it was found that a single i.m. injection of as little as 0.5 µg V1J:gD DNA elicited a neutralizing antibody response to gD that afforded statistically significant protection against lethal HSV challenge. Immunization with as little as 3.13 µg of the DNA in a two-dose regimen protected all animals from death.

EXAMPLE 9
Vaccination of Guinea Pigs with HSV PNV

Hartley strain guinea pigs (Harlan Sprague Dawley Labs, Indianapolis, Ind.) weighing approximately 200–250 grams each were vaccinated intramuscularly 0.1 ml in the right thigh and 0.1 ml in the left thigh at 11 and 4 weeks prior to virus challenge. Fresh solutions of the vaccine and placebo were sent to us for each vaccination.

In order to determine HSV-2 antibody production in the animals, the guinea pigs were bled 5 weeks after the first vaccination and 2 weeks after the second vaccination. Blood (0.6–1 ml per animal) was obtained by toe clipping. The blood was collected in microseparation tubes (Becton Dickinson), and was later centrifuged at 1000×g for 10 minutes to separate the serum.

The sera collected from the guinea pigs was analyzed for the presence of anti-HSV antibodies using the ELISA set forth in Example 6. The results are shown in Table 5.

TABLE 5

10 WEEK GUINEA PIG SERA ELISA gD

| Treatment | GMT | SEM (range) |
| --- | --- | --- |
| saline | 3 | 3–3 |
| 10 ug DNA | 19 | 8–43 |
| 100 ug DNA | 599 | 277–1295 |

At the time of infection, the guinea pigs weighed 600–700 grams each. They were infected intravaginaly with herpes simplex virus type 2 (HSV-2), E194 strain. This was accomplished in a 3-step process. First, the vagina of each animal was swabbed for 5 seconds with a cotton tip applicator dipped in 0.1 N NaOH. This treatment irritates the vaginal area so that the infection takes better. Approximately 45–60 minutes later each vagina was dry swabbed for 5 seconds. Then an applicator dipped in virus medium (about $5 \times 10^6$ plaque forming units of HSV-2 per ml) was used to swab each guinea pig for 20 seconds. The swabs were gently and slowly twisted back and forth during the time they were in place.

Lesion scores in infected animals were determined daily at day 2–15 post infection. A score of 1+ indicates about 25% of the anal-vaginal area was affected (usually by redness immediately around the vagina); 2+ indicates 50% of the anal-vaginal area affected; 3+ indicates 75% affected; and 4+ indicates 100% affected. Because some of the animals went on to die, the lesion score near the time of death carried through to the end of the 15 days. If this were not done, average lesion scores would appear to go down since the most affected animals died off.

Deaths were recorded daily for 21 days. The mean day of death calculation took into account only guinea pigs that die. Numbers of animals with hind limb paralysis were noted throughout the infection. Vaginal virus titers were made by titration of virus obtained from vaginal swabs at 2, 4 and 6 days after virus inoculation. The swabs were placed into tubes containing 1 ml of cell culture medium. The titration of these samples was conducted in Vero cells in 96-well plates. Calculation of virus titer was made by the 50% endpoint dilution method of Reed L. J. and Muench M., *Am. J. Hyg.* 27, 493–498 (1938). Virus titers were expressed as $log_{10}$ cell culture infectious doses per ml.

Statistical interpretations of survival (Fisher exact test), mean days to death (Mann-Whitney U test), paralysis (Fisher exact test), vaginal virus titers (Mann-Whitney U test), and vaginal lesion scores (Mann-Whitney U test) were made by two-tailed analyses.

FIG. 8 shows the results of survival, mean days to death, paralysis, and vaginal virus titers in HSV-2 infected guinea pigs. The high dose of vaccine prevented mortality and reduced vaginal virus titers on days 2 and 4 relative to the placebo control. The high dose of vaccine significantly prevented paralysis in these animals. The low dose of vaccine also reduced the above parameters.

Figure 9:
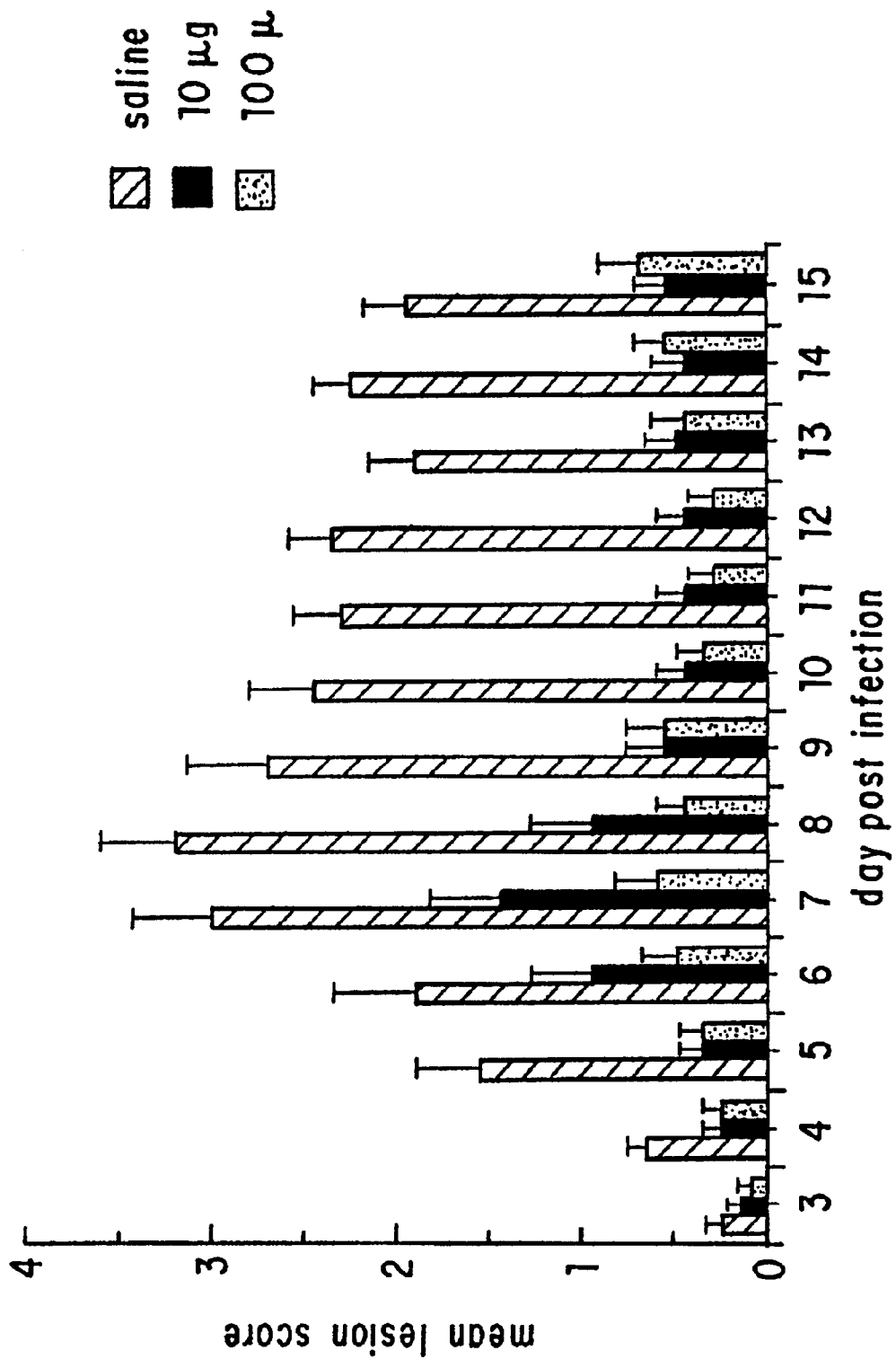

Table 6 shows daily vaginal lesion scores for the experiment. Both the high and low doses of the vaccine caused significant reductions in vaginal lesion severity from days 3 through 15 of the infection compared to the placebo group. The results in Table 6 are presented graphically in FIG. 9.

These results clearly indicate that the vaccine was protective in guinea pigs infected with HSV-2, and that the high dose of vaccine was more active than the low dose. The high dose of vaccine was not able to completely block the infection, since virus was recovered from vaccinees and a low grade of vaginal lesion development occurred. Nevertheless, the degree of protection afforded by the vaccine at this dose was substantial. The results of the antibody studies correlate with antiviral protection.

The vaccine administered intramuscularly at two different doses to guinea pigs 11 and 4 weeks prior to intravaginal HSV-2 challenge significantly protected animals from the disease. The high dose of vaccine was more effective than the low dose. The vaccine appears to be safe in the animals.

TABLE 6

| Day[b] | Vaccine[a], 10 μg | Vaccine[a], 100 μg | Placebo |
|---|---|---|---|
| 3 | 0.2 ± 0.2 | 0.1 ± 0.2 | 0.3 ± 0.3 |
| 4 | 0.2 ± 0.3* | 0.3 ± 0.4* | 0.7 ± 0.3 |
| 5 | 0.4 ± 0.4** | 0.4 ± 0.4** | 1.6 ± 1.1 |
| 6 | 1.0 ± 1.0 | 0.5 ± 0.6* | 1.9 ± 1.4 |
| 7 | 1.5 ± 1.2* | 0.6 ± 0.7*** | 3.0 ± 1.3 |
| 8 | 1.0 ± 1.0** | 0.5 ± 0.5*** | 3.2 ± 1.3 |
| 9 | 0.6 ± 0.7*** | 0.6 ± 0.7*** | 2.7 ± 1.4 |
| 10 | 0.5 ± 0.5*** | 0.4 ± 0.5*** | 2.5 ± 1.1 |
| 11 | 0.5 ± 0.5*** | 0.3 ± 0.4*** | 2.3 ± 0.8 |
| 12 | 0.5 ± 0.4*** | 0.3 ± 0.4*** | 2.4 ± 0.7 |
| 13 | 0.5 ± 0.5*** | 0.5 ± 0.6*** | 2.3 ± 0.8 |
| 14 | 0.5 ± 0.6*** | 0.6 ± 0.6*** | 2.3 ± 0.6 |
| 15 | 0.5 + 0.6*** | 0.7 + 0.7*** | 2.0 + 0.7 |
| Grand Avg. (Days 3–15) | 0.6 + 0.4*** | 0.4 + 0.2*** | 2.1 + 0.8 |

[a]Intramuscular vaccinations were given 11 and 4 weeks before virus challenge.
[b]After virus inoculation.
*$P < 0.05$, $P < 0.01$, *$P < 0.001$.

EXAMPLE 10

To determine whether mice vaccinated intramuscularly with PNV HSV would produce mucosal HSV-specific antibodies, mice were vaccinated with 12.5 or 1.56 μg of V1JNS:gD. Vaginal fluid was collected by swab and the antibodies were eluted from the swab using phosphate buffered saline. The eluant was analyzed for the presence of IgG and IgA, specific for HSV-2 protein. The ELISA was performed as described above except that commercially available antibodies specific for mouse IgG (Boehringer) and specific for mouse IgA (Seralab) were used to detect the presence of HSV-specific IgG and IgA in the mouse vaginal samples. The results for IgG are shown in Table 7; IgA was not detected in any animal.

TABLE 7

| Animal | ELISA Development Time (minutes) | |
|---|---|---|
| No. | 30 | 60 |
| 1031[a] | <0.1 | <0.1 |
| 1032[a] | 0.1 | 0.1 |
| 1033[a] | 0.01 | 0.01 |
| 1035[a] | <0.1 | 0.1 |
| 1037[b] | <0.1 | <0.1 |
| 1038[b] | <0.1 | <0.1 |
| 1039[b] | <0.1 | <0.1 |
| 1040[b] | <0.1 | <0.1 |

[a]immunized once with 12.5 μg V1JNS:gD
[b]immunized once with 1.56 ug V1JNS:gD

EXAMPLE 11

DNA vaccines expressing herpes simplex virus type 2 (HSV-2) full-length glycoprotein D (gD), or a truncated form of HSV-2 glycoprotein B (gB) were evaluated for protective efficacy in two experimental models of HSV-2 infection. Intramuscular (i.m.) injection of mice showed that each construction induced neutralizing serum antibodies and protected the mice from lethal HSV-2 infection. Dose-titration studies showed that low doses ($\leq 1$ μg) of either DNA construction induced protective immunity, and that a single immunization with the gD construction was effective. The two DNAs were then tested in a low-dosage combination in guinea pigs. Immune sera from DNA-injected animals had antibodies to both gD and gB, and virus neutralizing activity. When challenged by vaginal infection with HSV-2, the DNA-immunized animals were significantly protected from primary genital disease.

Virus was routinely prepared as indicated in Example 3. Briefly, virus was routinely prepared by infection of nearly confluent Vero or BHK cells with a multiplicity of infection (m.o.i.) of 0.1 at 37° C. in a small volume of cell-culture medium without serum. After one hour, virus inoculum was removed and cultures were re-fed with high glucose DMEM supplemented with 2% heat inactivated fetal bovine serum (FBS), 2 mM L-glutamine, 25 mM HEPES, 50 U/mL penicillin and 50 μg/mL streptomycin. Incubation was continued until cytopathic effect was extensive: usually for 24 to 48 hrs. Cell-associated virus was collected by centrifugation at 1800×g 10 min., 4° C. Supernatant virus was clarified by centrifugation at 640×g for 10 min., 4° C., and stored at −70° C.

Female BALB/c mice (Charles River Laboratories; Wilmington, Mass.) and female Duncan Hartley guinea pigs (Harlan Sprague Dawley; Indianapolis, Ind.) were maintained and utilized in accordance with Institutional Animal Care and Use Committee-approved protocols.

HSV-2 strain Curtis DNA, used as template for polymerase chain reactions (PCR) as disclosed in Example 4. A 1,182 base pair (bp) fragment encoding the gD precursor gene was amplified by PCR (Perkin Elmer Cetus; La Jolla, Calif.) using synthetic oligonucleotide primers (Midland Certified Reagent Company; Midland, Tex.) which corresponded to 5' and 3' end flanking sequences for the HSV-2 gD gene and contained Bgl II restriction sites. A 2,121 bp sequence encoding the amino-terminal 707 aa of HSV-2 gB was amplified by PCR. Primers corresponding to the 5' flanking sequence, and complementary to nucleotides 2,110 to 2,121 (FIG. 3, Stuve, et al., 1987, *J. Virol.* 61: 326–335) were used to generate Bgl II restriction sites flanking the coding sequence, and to add the termination codon TAA immediately after nucleotide 2,121. Bgl II-digested PCR-amplified fragments were ligated into vectors V1J or V1Jns (see Example 1 and Example 2). *E. coli* DH5a (BRL-Gibco) was transformed according to the manufacturer's specifications. Candidate plasmids were characterized by restriction mapping, and the vector-insert junctions were sequenced using the Sequenase DNA Sequencing Kit, version 2.0 (United States Biochemical; Cleveland, Ohio). The gD-coding sequence, originally cloned in V1J, was subcloned into V1Jns. For simplicity, in this Example 11 the final gD and truncated gB plasmid constructions were designated gD-2 and ΔgB-2, respectively. Large-scale DNA preparations were essentially as described in Example 4.

Plasmid DNA was precipitated onto rhabdomyosarcoma (RD) cells (ATCC CCL136) by the calcium phosphate method using Pharmacia CellPhect Kit (Pharmacia Biotech Inc.; Piscataway, N.J.) reagents according to the manufacturer's instructions except that 5 or 15 μg of DNA/well were used. After 48 hrs., cell lysates were resolved by electrophoresis and then transferred to nitrocellulose membranes. Immunoblots were processed with an anti-HSV gD monoclonal antibody (Advanced Biotechnologies Inc.; Columbia, Md.) or sheep anti-HSV-2 antiserum (ViroStat; Portland, Me.) and developed with the ECL detection kit (Amersham; Arlington Heights, Ill.).

In regard to animal immunization, in all cases "DNA dose" refers to the total amount of DNA injected per animal per round of immunization; half the total was delivered to each injection site. Mice were anesthetized by intraperitoneal (i.p.) injection of a mixture of 2 mg ketamine HCl (Aveco; Fort Dodge, Iowa) and 0.2 mg xylazine (Mobley Corp.; Shawnee, Kans.) in saline. The hind legs were shaved with electric clippers and washed with 70% ethanol. Each quadriceps muscle was injected with 50 μL of DNA diluted into sterile saline just prior to use. Control animals were sham-immunized with saline or vector DNA. Mice were five to six weeks old at the time of the first immunization. Guinea pigs, weighing 400–550 gm at the time of the first immunization, were anesthetized by subcutaneous injection of 22 mg ketamine plus 5 mg xylazine/kg; the hind legs were washed with 70% ethanol and each quadriceps muscle was injected i. m. with 100 μL of DNA or saline. Sera were assayed for HSV-specific responses in ELISAs using either HSV glycoproteins partially purified from HSV-2 Curtis-infected BHK cell lysates (mouse sera) or recombinantly-expressed gD and ΔgB purified from recombinant baculovirus-gD and baculovirus-gB infected SF21 cultures (guinea pig sera). Recombinant viruses were constructed using the BacPAK Baculovirus Expression System (Clontech; Palo Alto, Calif.) pBacPAK8 transfer vector and Bsu361 digested BacPAK6 virus, and gD and ΔgB coding sequences from gD-2 and ΔgB-2, respectively. Glycoproteins from HSV-2 or baculovirus-gD infected cultures were purified by Lentil Lectin Sepharose chromatography (Pharmacia Biotech Inc) essentially as described (Pachl, et al., 1987, *J. Virology* 61: 315–325). Truncated glycoprotein B was purified from clarified culture medium adjusted to 0.1 mM $MnCl_2$, 0.5% NP40, batch adsorbed at room temperature to Lentil Lectin Sepharose 4B and eluted as previously described. For the ELISA, glycoproteins were diluted to 5 μg/mL total protein in 50 mM carbonate buffer (pH 9.5), 100 μL/well was applied to Maxi-sorb 96-well plates (Nunc; Naperville, Ill.) and allowed to absorb at 4° C., overnight. All subsequent incubations were carried out in 100 μL volumes for 1 hour at room temperature and plates were washed four times with phosphate buffered saline (PBS, pH 7.2) with or without one distilled water wash between steps. Dilution buffer (920 mM Tris-HCl [pH 7.5], 137 mM NaCl, 2.7 mM KCl, 0.5% gelatin, 0.05% Tween 20) was used as a blocking agent as well as for the serial dilution of immune sera and the dilution of alkaline phosphatase-labeled goat anti-mouse (Boehringer Mannheim; Indianapolis, Ind.), or goat anti-guinea pig (Accurate Chemical and Scientific Corp., Westbury, N.Y.). The ELISA was developed with 1 mg/mL p-nitrophenylphosphate in 10% diethanolamine (pH 9.8), 0.5 mM $MgCl.6 H_2O$ at 37° C. and optical absorbance was read at 405 nm. Serum dilutions were scored as positive if the $OD_{405}$ signal exceeded by more than three standard deviations the mean $OD_{405}$ signal (six replicates) of sera from sham-immunized mice at the same dilution, or if the $OD_{405}$ signal exceeded by >0.1 OD units, the signal of the guinea pig's preimmune serum at the same dilution. The reciprocal of the last sample dilution scored positive was taken as the endpoint titer. Individual endpoint titers were used to calculate geometric mean titers (GMT). For purposes of calculation, sera negative at the lowest dilution tested were assigned endpoint titers equal to the reciprocal of the next lower dilution if the dilution series had been extended. ELISA titers are HSV-specific as originally shown by lack of measurable ELISA titer in sera from naive or saline-immunized animals, and by the lack of reaction of immune sera with antigen prepared from mock-infected BHK cell lysates.

HSV neutalization took place essentially as described in Example 7. Briefly, sera from DNA- or saline-immunized animals were heat inactivated at 56° C. for 30 min. prior to serial dilution in DMEM, 2% heat-inactivated FBS; 50 μL of each dilution were delivered to duplicate wells in a sterile polypropylene 0.5 mL 96 well plate (Marsh Biomedical; Rochester, N.Y.). HSV-2 stocks were diluted to 4,000 plaque forming units (pfu)/mL; 50 μL of virus was added to sample wells and the plate incubated overnight at 4° C. Guinea pig complement (Cappel; Durham, N.C.) was diluted 1:4 in DMEM, 2% heat inactivated FBS; 50 μL was added to each sample well. After a one hour incubation at 37° C., 100 μL of serum-free medium was added and then each reaction mixture was used to infect confluent Vero cells in 12-well cluster plates (Costar) incubated for one hour at 37° C. Inocula were aspirated, monolayers were overlaid with 1 mL 1× MEM containing 5% heat inactivated FBS, 1× Basal Medium Eagle vitamins, 10 mM L-glutamine, 25 U/mL penicillin, 25 μg/mL streptomycin, 12.5 mM HEPES, 0.5% carboxymethylcellulose and plates were incubated at 37° C. for 48 hours. Monolayers were stained with 1% basic fuchsin in 50% methanol, 10% phenol and the number of plaques determined. A serum dilution was considered neutralization positive if plaque numbers were ≦50% of those obtained in parallel control assays using pooled sera from saline-immunized control mice or preimmune serum from the same guinea pig at the same dilution.

Mouse survival data were analyzed using the log-rank test in the SAS® procedure LIFETEST (Lee, E. T., 1980, *Statistical methods for survival data analysis*; Lifetime Learning Publications, Belmonth, Calif., p. 122–156.). Guinea pig daily lesion scores were analyzed by the two-tailed Student's t test. For comparison of overall disease among groups of guinea pigs, mean lesion scores were analyzed by the Kruskal-Wallis test followed by a multiple comparison test at the $p<0.05$ significance level.

The coding sequences for full-length gD and the amino-terminal 707 aa of gB were cloned from HSV-2 strain Curtis viral DNA by PCR methods into the eukaryotic expression vectors V1J or V1Jns, described at length in Examples 1 and 2, and are designated gD-2 and ΔgB-2, respectively, for the purpose of Example 11. As noted in the disclosure, expression is similar from V1J, V1Jneo and V1Jns. The plasmids were characterized by restriction mapping and sequence analysis of the vector-insert junctions. Over the regions sequenced, the gD clone was identical with that published for HSV-2 strain G (Lasky and Dowbenko, 1984, *DNA* 3: 23–29) and the gB clone sequence was identical with that published for HSV-2 strain 333 (Stuve, et al., 1987, *J. Virol.* 61: 326–335.). The ability of gD-2, or ΔgB-2 plasmids to express the encoded protein was demonstrated by transient transfection of RD cells. Immunoblot analysis of gD-2 DNA-transfected RD-cell lysates with an anti-HSV-2 gD monoclonal antibody detected a protein with a MW of approximately 60 K not present in mock-transfected RD cell lysates. Immunoblot analysis of conditioned medium from ΔgB-2 DNA-transfected RD cells and cell lysates with sheep anti-HSV-2 antiserum detected a protein with an apparent MW of 106 K not present in controls, and found that a majority of the protein was in the medium. The observed size was consistent with a 707 aa truncated form of gB and because this truncation deleted the transmembrane and cytoplamic domains from HSV-2 gB the expressed protein was not expected to be cell associated.

The biological effects of immunization with gD-2 or ΔgB-2 DNA were investigated in separate dose-titration experiments in mice. Animals were immunized by i. m. injection of DNA or were sham-immunized with saline at weeks zero and seven. Sera obtained at week ten were assayed in an HSV-specific ELISA. Table 8 shows the seroconversion results and reports the geometric mean titers (GMT) ± the standard error of the mean (SEM) attained for each dose group. In these assays, pooled sera from the saline-injected control mice were used as the negative controls. The results indicated that injection of each DNA constructions resulted in protein expression in vivo and the induction of substantial antibody responses, even at low doses. At the lowest dose tested, 0.8 μg gD-2 DNA, eight of nine immunized mice developed detectable antibody responses.

Representative sera from both gD-2 DNA- and ΔgB-2 DNA-immunized animals were surveyed for HSV-2 (strain Curtis) neutralizing activity at dilutions of 1:10, 1:100, and 1:1000. Fifteen sera from mice injected with doses of gD-2 DNA ranging from 3.1 to 100 μg were tested; thirteen were neutralization positive at 1:10; of those, eleven were also positive at 1:100; and of those, five were positive at the 1:1,000 dilution. The two negative sera (from the 50 μg dose group) also had low ELISA endpoint titers ($\log_{10} \leq 2.00$ and 2.52, respectively). A more limited survey of sera from the animals immunized with 30 μg ΔgB-2 DNA found that of three sera tested, all were positive at 1:10, two at 1:100, and none at 1:1000. These results indicated that immunization with either DNA construction was capable of inducing HSV-2 neutralizing antibodies in mice.

Figure 10A:
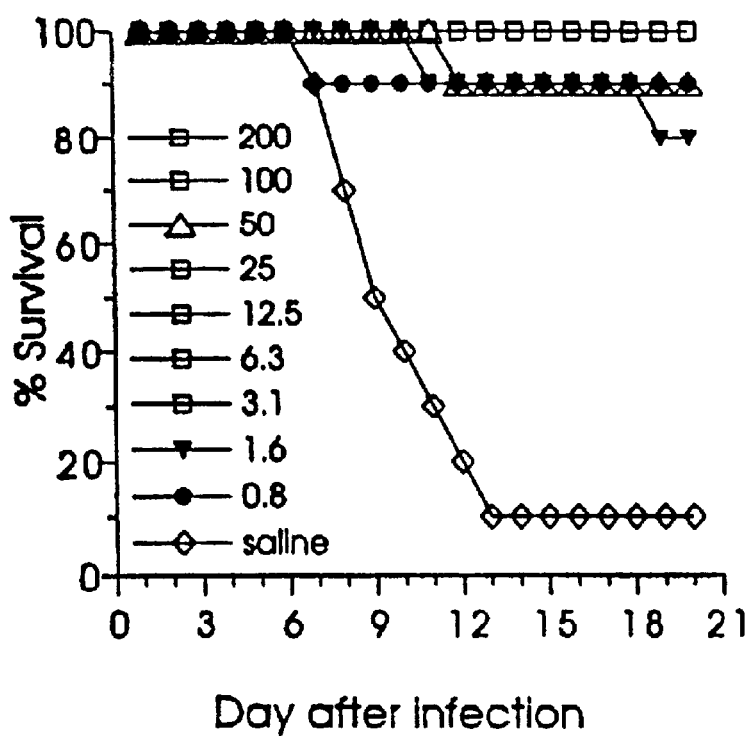
Figure 10B:
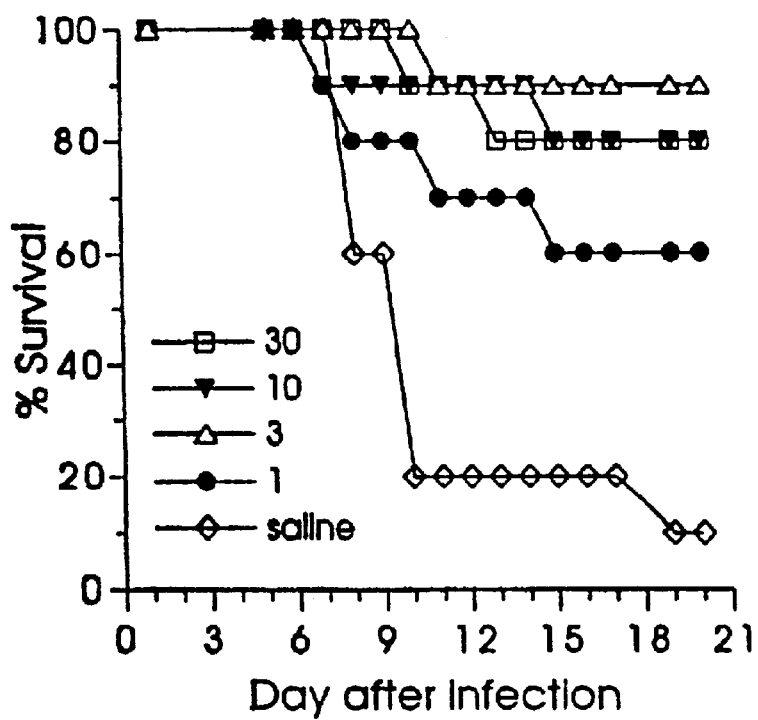

Immunized and control (saline-injected) mice were challenged by i.p. injection of of HSV-2 and observed daily for survival. FIG. 10A shows the effect of gD-2 DNA immunization on survival; significant protection from death ($p < 0.001$) was achieved for each dose. Eighty-two of eighty-six gD-2 DNA immunized mice survived challenge. The survival results for the ΔgB-2 DNA-immunized mice are in FIG. 10B. A significant protection from death was found for each dose tested ($p < 0.01$ for the 30, 10, and 3 μg groups, and $p = 0.027$ for 1 μg group). Thus, low dose immunization with either gD-2 or ΔgB-2 DNA induced antibody responses in mice which protected them from lethal HSV-2 infection. During the observation period, some animals exhibited transient morbidity: failure to groom, failure to thrive, or a hunched posture. Infection was confirmed in some animals by the detection of antibodies to nonstructural HSV proteins in convalescent sera.

Figure 11:
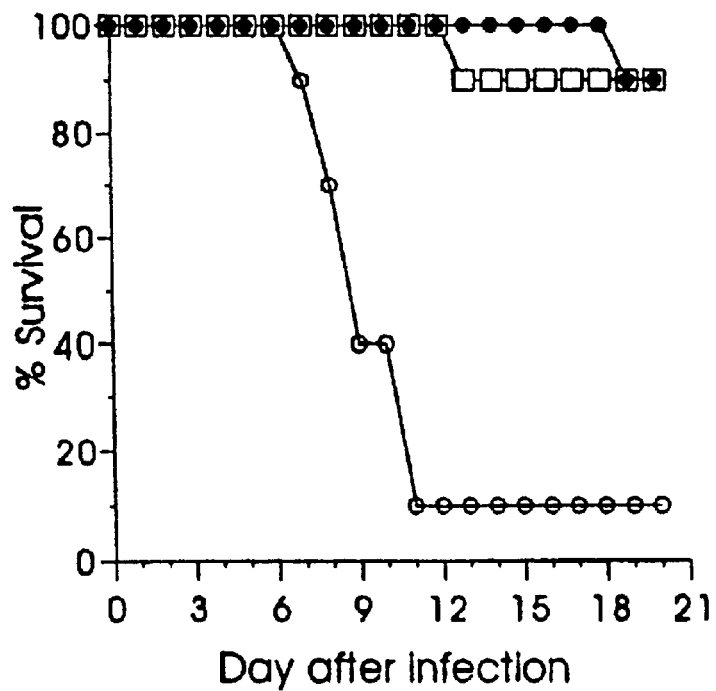

Sham immunization with saline was used as the control in dose-titrations. To confirm that protection was dependent upon the HSV coding sequence rather than injection of DNA per se, groups of ten mice were immunized with either 12.5, or 1.6 μg gD-2 DNA, or 12.5 μg of vector V1J DNA. Ten weeks after a single immunization, sera were analyzed by ELISA. The $\log_{10}$ GMT (±SEM) for the group injected with 12.5 μg gD-2 DNA was 3.89 (0.97) and that for the 1.6 μg group was 2.49 (1.20). None of the sera from mice immunized with vector DNA were seropositive; the $\log_{10}$ GMT of 0.48 was background. FIG. 11 reports the survival data for these animals following i.p. challenge at eleven weeks. Both groups immunized with gD-2 DNA were significantly protected from compared to those immunized with the vector death ($p < 0.001$). Survival of the vector-injected animals was similar to that found for the saline-injected animals in the experiments summarized in FIG. 10. These results confirmed that protection was dependent upon the gD coding sequence. Furthermore, they demonstrated that protective immunity could be established with a single injection of gD-2 DNA. Additional studies in mice and guinea pigs (see Example 12) comparing plasmids ΔgB-2 or gD-2 with vector, or with control plasmids that expressed influenza viral proteins, also found that protection was dependent on the presence HSV protein-coding sequences.

The lethal infection model was useful for confirming the in vivo activity of the gD-2 and ΔgB-2 DNA, and for establishing that low DNA doses were effective. However, to more closely mimic a human disease state, a guinea pig vaginal infection model was used to assay the effects of immunization with a combination of low doses of gD-2 and ΔgB-2 DNA. Seven guinea pigs were immunized with a DNA mixture containing 3 μg gD-2 DNA and 10 μg ΔgB-2 DNA at weeks zero and six; fourteen control guinea pigs were sham-immunized with saline. Sera, obtained at nine weeks were analyzed for anti-gD and anti-gB antibodies using antigen-specific ELISAs. Results are shown in Table 9. All of the DNA-immunized animals developed ELISA titers to both gD and gB; individual endpoint titers were $\geq 300$. None of the sham-immunized animals were positive at the lowest dilution (1:30) tested. The results indicated that both DNAs in the mixture were expressed. These sera were also assayed for HSV-2 neutralizing antibodies. Immune sera from all seven DNA-immunized animals were neutralization positive at a 1:10 dilution, six of seven at 1:100, two at 1:1,000, and none at 1:10,000. None of four randomly-selected representative sera from the sham-immunized control animals were positive at dilutions of 1:10 or 1:100.

At ten weeks, all of the DNA-immunized, and eight of the sham-immunized guinea pigs were challenged by introduction of HSV-2 strain MS into the vagina. As a control for any effect the manipulations used in the infection procedure might have on the scoring of external disease, the remaining six sham-immunized animals were mock-infected using an inoculum prepared from mock-infected Vero cells. The severity of the primary disease was assessed by the lesion scoring system described in the legend to FIG. 12. The course of primary disease is summarized in FIG. 12 by reporting the mean daily lesion scores on days three through fourteen following infection. All animals in the infected control group developed severe external disease. From day five onward, this group's scores were significantly higher than those of the DNA-immunized, or the mock-infected control groups ($p < 0.01$). In contrast, none of the DNA-immunized animals developed severe disease, and the scores for this group were statistically indistinguishable from those of the mock-infected group. The overall primary disease, as measured by the means of all lesion scores, was significantly lower for the DNA-immunized group compared to the infected control group ($p < 0.001$) but was not significantly different from the mock-infected control group ($p = 0.92$). The scores for the mock-infected group were taken as the experimental background.

Figure 12:
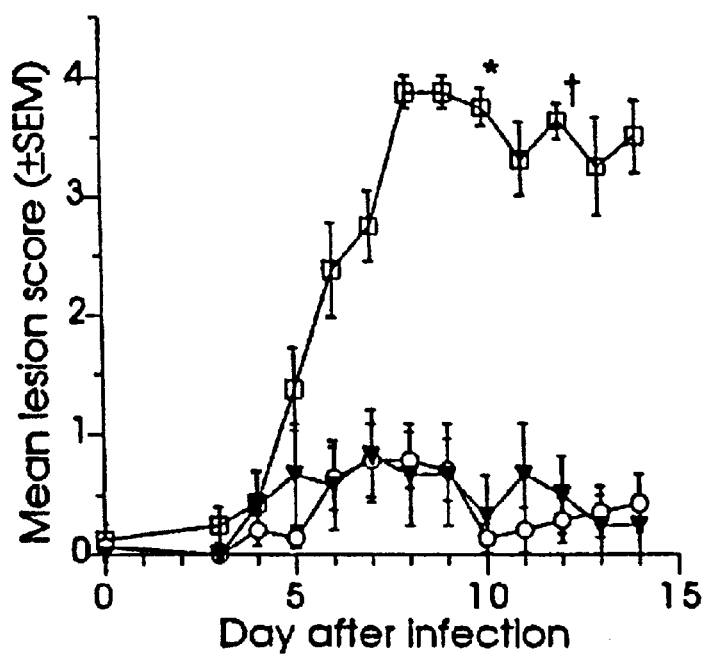
Figure 13A:
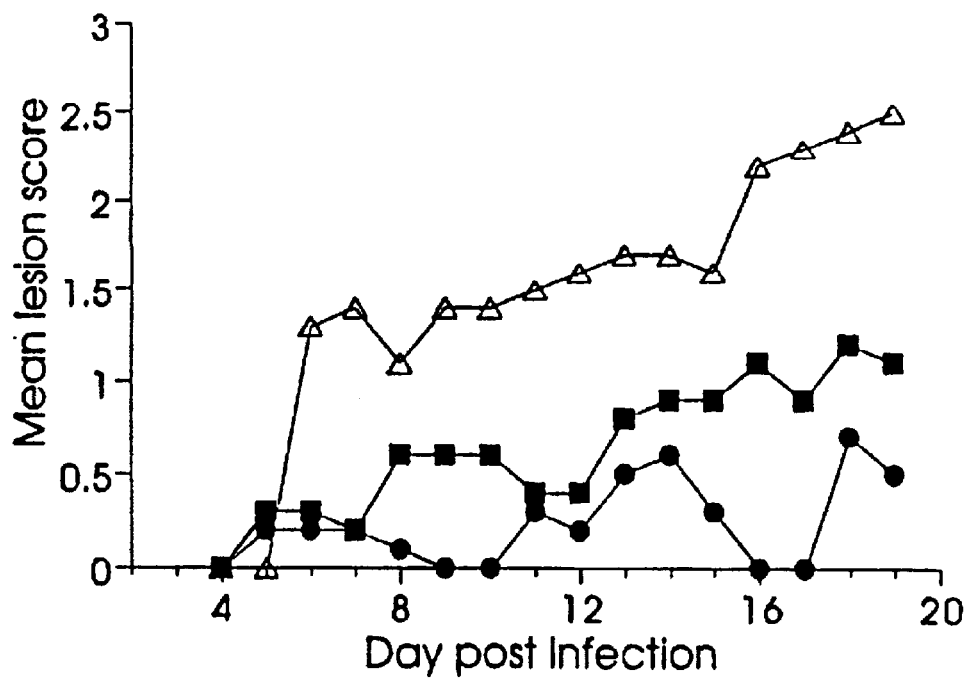
Figure 13B:
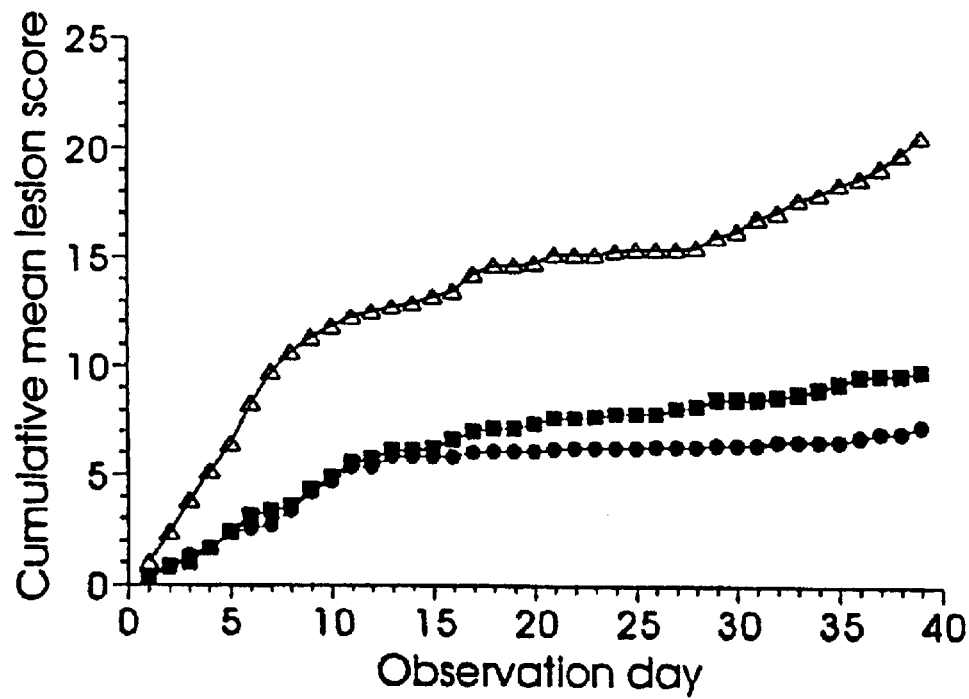

The DNA-immunized animals were further distinguished from the infected controls in that none of them developed signs of systemic disease. In contrast, six of the eight sham-immunized infected guinea pigs showed signs of severe systemic infection: five retained urine on two or more days, one developed partial paralysis of the hind limbs, and five animals became moribund during the observation period and required euthanization (FIG. 12). None of the mock-infected animals showed signs of systemic disease. Th challenge study of this Example indicates that immunization with low doses of DNAs which encode HSV-2 full-length gD and a truncated form of gB protected guinea pigs from HSV-2-induced primary genital disease.

The data show that immunization with DNA encoding full-length HSV-2 gD or a truncated form of HSV-2 gB induced immune responses in mice and protected them from lethal challenge with HSV-2, and that a combination of these two DNAs at low doses protected guinea pigs from primary genital disease. This protection was generated with low doses of DNA, and in the mice model with a single immunization.

When gD-2 DNA was titrated over a 250-fold concentration range in mice, all doses tested induced serum antibodies and protected mice from lethal infection. The level of protection induced by the 0.8 μg dose could not be distinguished statistically from that induced by the highest dose tested. In subsequent titration studies, a single injection of as little as 50 ng of gD DNA could induce detectable antibody responses although doses of 500 ng were required to obtain consistent seroconversion, and that a single immunization with 1.6 μg gD-2 DNA protected mice from lethal i.p. challenge (FIG. 11). Titration of ΔgB-2 DNA in mice showed that two immunizations with as little as 1 μg resulted in significant protection. A preferred, but not limiting, range for a combination polynucleotide vaccine expressing ΔgB and gD is 2.0 μg gD and 0.6 μg ΔgB, respectively, in a guinea pig model.

It has been postulated that due to competition for DNA uptake or expression, or antigen competition, immunization with DNAs in combination might result in reduced responses to the individual components. The combination of gD-2 and ΔgB-2 DNA did not appear to compromise the response to either component. Moreover, the protection achieved with this low-dosage combination was as good as, or better than that seen in similar challenge studies using 100 μg doses of gD-2 DNA or ΔgB-2 DNA alone. Because the combination of gD-2 and ΔgB-2 DNA could induce responses to the broader spectrum of epitopes contained in two separate antigens, it had the potential to be more effective than either component alone. The results are consistent with the combination being more effective than the individual components; but, that can not be concluded from this study since the comparison was not made directly. Further titrations of gD-2 DNA and ΔgB-2 DNA, both individually and in combination are in progress to address the question directly, and to establish minimally-effective doses.

This Example shows that immunization with low doses of DNA is highly effective in generating protective immunity in two animal models of HSV infection, and in mice, that a single immunization was protective. These results show that an i. m. injection has the potential to be an efficient form of DNA delivery, and support the feasibility of developing DNA vaccines for human use where low dose and limited numbers of injections are desirable characteristics. The combination of gD-2 and ΔgB-2 DNA induced immune responses to both proteins and was effective in preventing HSV-2-induced mucosal disease. This result supports the idea that multivalent vaccines can be made by simply combining DNAs.

TABLE 8

Effect of DNA immunization on antibody development in mice

| DNA Dose (μg)* | number seropositive | n† | GMT($\log_{10}$) | ±(SEM) |
|---|---|---|---|---|
| gD-2 | | | | |
| 200 | 9 | 9 | 4.44 | (.22) |
| 100 | 10 | 10 | 4.69 | (.31) |
| 50 | 9 | 10 | 4.38 | (.33) |
| 25 | 8 | 8 | 4.26 | (.23) |
| 12.5 | 10 | 10 | 4.15 | (.30) |
| 6.3 | 10 | 10 | 4.21 | (.33) |
| 3.1 | 10 | 10 | 3.89 | (.18) |
| 1.6 | 7 | 10 | 2.56 | (.35) |
| 0.8 | 8 | 9 | 3.75 | (.43) |

TABLE 8-continued

Effect of DNA immunization on antibody development in mice

| DNA Dose (μg)* | number seropositive | n† | GMT($\log_{10}$) | ±(SEM) |
|---|---|---|---|---|
| saline | | | (0.48)‡ | |
| ΔgB-2 | | | | |
| 30 | 10 | 10 | 4.88 | (.16) |
| 10 | 10 | 10 | 4.58 | (.18) |
| 3 | 10 | 10 | 4.47 | (.15) |
| 1 | 10 | 10 | 4.18 | (.15) |
| saline | | | (0.48)‡ | |

*dose given at weeks 0 and 7; sera obtained at week 10,
†number of sera tested,
‡By convention, pooled sera from saline-injected mice were defined as negative at all dilutions tested and assigned endpoint titers equal to the reciprocal of the next lower dilution had the series been extended; in these cases 1:3.

TABLE 9

Effect of immunization with a combination of gD-2 and ΔgB-2 DNA on antibody development in guinea pigs.

| immunization | n* | no. positive sera | | $\log_{10}$ ELISA GMT ± (SEM) | |
|---|---|---|---|---|---|
| | | anti-gD | anti-gB | anti-gD | anti-gB |
| gD-2 + ΔgB-2 DNA | 7 | 7 | 7 | 2.62 (.14) | 3.05 (.20) |
| saline | 14 | 0 | 0 | 0.48 (0)† | 0.48 (0)† |

*number of animals
†For purposes of GMT calculation, sera negative at all dilutions tested were assigned an endpoint titer equal to the reciprocal of the what would have been the next lower dilution had the dilution series been extended; in this case 1:3.

EXAMPLE 12

As in Example 11, plasmid expression vectors encoding herpes simplex virus type 2 (HSV-2) glycoproteins B (gB) or D (gD) were constructed and tested for their ability to immunize guinea pigs against genital HSV infection. Immunization with a plasmid expressing the amino-terminal 707 amino acids (aa) of gB induced humoral immune responses detected by ELISA and virus neutralization. When challenged by vaginal infection, immunized animals were partially protected from genital herpes, exhibiting significantly reduced primary and subsequent recurrent disease. When the gB plasmid was combined with a plasmid expressing full-length gD, immunized guinea pigs developed humoral responses to both proteins and were also significantly protected from viral challenge.

Plasmid vectors expressing full-length gD, or a carboxy-terminal deleted form of gB were constructed using the expression vector V1Jns, a derivative of the vector V1J, as described throughout this specification in general and Example 11 in particular. Expression, in this vector, is driven by the cytomegalovirus immediate early (CMVIE) protein promoter. Sequences encoding gD or gB were PCR-amplified from HSV-2 strain Curtis viral DNA. Expression of the full-length, 393 amino acids (aa) gD from plasmid V1Jns:gD was confirmed by immunoblot analysis of transiently-transfected human embryonal rhabdomyosarcoma (RD) cells using a gD-specific monoclonal antibody. Indirect immunofluorescence indicated that the expressed protein was associated with the cell membrane. The gB plasmid:V1Jns:ΔgB was constructed to express the amino-terminal 707 aa of the 904 aa-gB. This truncated protein has had the transmembrane and cytoplasmic domains of gB deleted and therefore, was expected to be secreted from transfected cells. Immunoblot analysis of transiently-transfected RD cells with sheep anti-HSV-2 antiserum (ViroStat) detected a protein of the expected size (106 kDa), the majority of which was found in the conditioned medium. The in vivo activities of these DNA constructions were confirmed by induction of gD-or gB-specific serum antibodies in mice, guinea pigs, and nonhuman primates upon im injection. All animal studies were carried out in accordance with Institutional Animal Care and Use Committee-approved protocols.

The effect of V1Jns:ΔgB plasmid (i.e., ΔgB-2 of Example 11) on genital HSV infection was studied by immunizing female Duncan Hartley guinea pigs (HRP Inc.) with 100 μg or 10 μg of V1Jns:ΔgB. Control animals were immunized with 100 μg of V1Jns:HA, a plasmid expressing influenza A virus hemagglutinin. The DNA was delivered in 200 μL of saline; 100 μL in each quadriceps muscle. At six weeks, all animals were reimmunized.

Sera obtained at ten weeks were analyzed by an HSV-specific ELISA which used partially purified HSV-infected baby hamster kidney cell lysate as capture antigen. The ELISA was originally qualified as HSV specific by the differential responses of sera from infected, immunized, or control mice and guinea pigs. Endpoint titers were taken as the reciprocal of the highest serum dilution which gave an $OD_{405}$ signal greater than three standard deviations above the mean $OD_{405}$ signal of six replicates of control-animal sera at the same dilution. All of the V1Jns:ΔgB-immunized animals were seropositive. The geometric mean titer ± the standard error (GMT±SE) for the 100 μg V1Jns:ΔgB group was 120,000±30,000; for the low (10 g) dose group it was 147,000±32,300. The GMT of the V1Jns:HA-immunized control group was 3.0±0 by definition. These sera were also assayed for complement-dependent virus neutralization. Dilutions of heat inactivated serum were incubated with 200 plaque forming units (pfu) of HSV-2 Curtis overnight at 4° C. Guinea pig complement was added for one hour at 37° C. before assaying for viable virus on Vero cells. The percent plaque reduction was determined (in duplicate) for each serum dilution compared to the same dilution of pre-immune serum, scoring a 50% or greater reduction in plaque number as positive. In an initial survey at dilutions of 1:10 and 1:100, sera from all V1Jns:ΔgB animals were positive at both dilutions; none of the sera from V1Jns:HA-immunized animals were positive. In an attempt to define endpoint titers, one serum from the 100 μg-dose group, four sera from the 10 μg-dose group, and one serum from the HA DNA-immunized group were chosen randomly for further titration. All five sera from the V1Jns:ΔgB-immunized pigs were neutralization positive at a 1:1,000 dilution and negative at 1:10,000; the control serum was negative at 1:10. Immune sera from these V1Jns:ΔgB-immunized guinea also neutralized HSV-1 strain KOS infectivity with approximately the same titers found for HSV-2 neutralization. Convalescent sera from control guinea pigs surviving vaginal infection with HSV-2 were neutralization positive at 1:1,000 but negative at higher dilutions. Thus, immunization with DNA expressing a truncated form of gB induced neutralizing antibody titers in guinea pigs similar to those found in infected animals.

Ten weeks after the initial immunization, the guinea pigs were challenged by inoculation of HSV-2 into the vagina. FIG. 13A summarizes the course of primary disease by reporting the mean of the daily lesion scores for each test group on days three through eighteen. By day five, the mean lesion scores of both the high- and low-dose V1Jns:ΔgB groups were reduced compared to the control. The reductions in overall disease were found to be significant by the repeated measures of variance analysis: $p<0.01$ for the 100 μg-dose V1Jns:ΔgB group and $p=0.04$ for the 10 μg-dose group. The incidence of severe disease (lesion scores≧3.0) was higher in the control group than in either test group, and during the course of the primary infection four (of ten) HA-DNA-immunized animals developed systemic disease, became moribund and were euthanized while two (of nine) 10 μg ΔgB DNA-immunized pigs required euthanization. All nine of the 100 μg-ΔgB DNA-immunized pigs survived.

Following primary infection guinea pigs, like humans, develop latent herpes infections which occasionally reactivate to cause recurrent disease. The surviving animals were observed for recurrent disease over a ten week period beginning four weeks after virus inoculation. Thirty-nine sets of observations were made, and disease was scored by the same scale used for primary disease. Because recurrent disease is usually less severe than the primary disease and because it can occur infrequently, recurrence data are presented in FIG. 13B as cumulative mean lesion scores for each observation day. This running tally of the daily mean lesion scores includes contributions from the frequency, severity, and duration of each recurrent episode. The figure shows that the control animals experienced significantly ($p=0.03$) more recurrent disease than either group immunized with ΔgB DNA. Not only were there quantitative differences, the curves indicate that while the control animals continued to have recurrences throughout the observation period, the animals immunized with 100 μg V1Jns:ΔgB were nearly free of recurrence from observation day 13. These results show that immunization with DNA encoding a truncated form of HSV-2 gB induced immune responses in guinea pigs which were associated with partial protection from primary and subsequent recurrent HSV-induced genital disease.

The V1Jns:ΔgB plasmid was tested in combination with the plasmid V1Jns:gD (i.e., gD-2 of Example 11), which expresses full-length HSV-2 gD. Guinea pigs were immunized twice with either a mixture of 100 μg V1Jns:ΔgB+100 μg V1Jns:gD, or with 100 μg V1Jns:HA by the regimen described above. At ten weeks, sera and vaginal secretions were obtained and analyzed by gD- and gB-specific ELISAs. These ELISAs used cloned, baculovirus-expressed gD or truncated gB proteins as capture antigens and were originally qualified as antigen-specific using sera from guinea pigs and mice immunized singly with V1Jns:gD or V1Jns:ΔgB. The V1Jns:ΔgB+V1Jns:gD-immunized guinea pigs were seropositive for both gD and gB; the GMTs for both responses were identical: 6,926±2,945 although individual animals responded differently to the two immunogens. The GMT for the V1Jns:HA-immunized control group was, by definition, 3±0. These results indicated that immunization of guinea pigs with a mixture of DNAs encoding gD and gB induced immune responses to both proteins.

Vaginal secretions were collected from seven of the V1Jns:ΔgB+V1Jns:gD-immunized guinea pigs by swabbing with saline-moistened calcium alginate swabs which were eluted into 1 mL of saline. All seven animals tested had detectable anti-gD responses; titers ranged from 2 to ≧8. Four of the seven animals had a detectable anti-gB response; titers were ≧8 in all cases. Secretions from the HA DNA immunized pigs were used as negative controls. In this same experiment, secretions from three animals immunized with a 100 μg of a plasmid expressing the HSV-2 transactivating protein VP16 were negative for anti-gD or -gB response when tested neat. These vaginal anti-gD and -gB antibodies were found to be IgG and may be the result of transudation of serum antibodies.

Figure 14A:
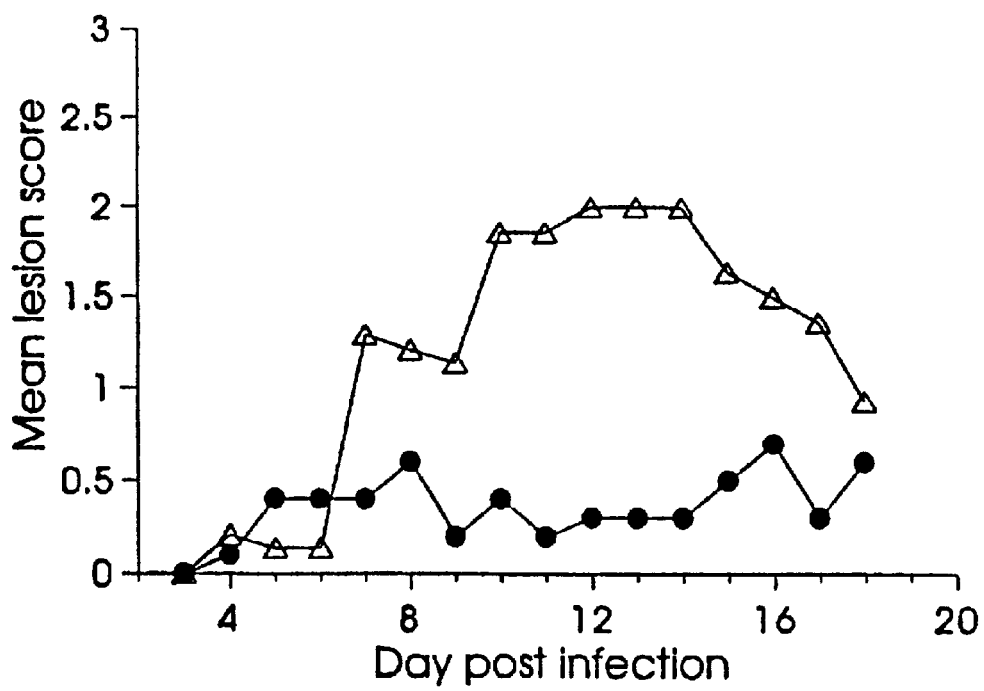
Figure 14B:
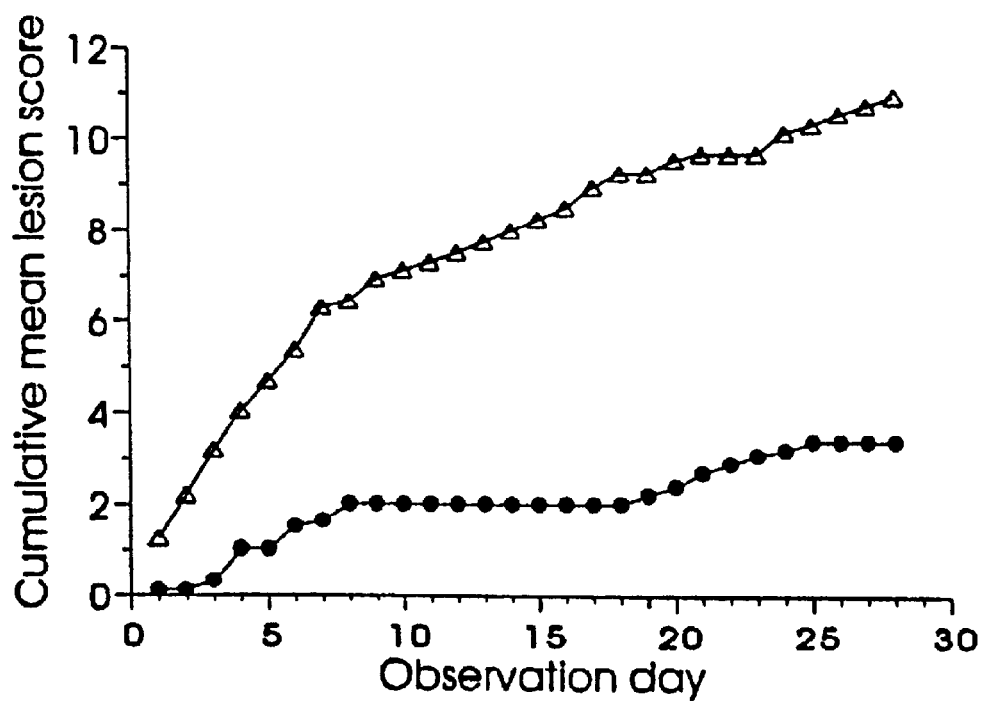

At ten weeks, the animals were challenged with HSV-2 and evaluated for primary and recurrent disease as described above. The course of primary infection is summarized in FIG. 14A. By day seven, the mean lesion scores for the V1Jns:ΔgB+V1Jns:gD group were substantially lower than those for the control group. Over the entire observation period, the reduction was significant; p<0.001. None of the eight V1Jns:ΔgB+V1Jns:gD-immunized group developed severe disease (lesion scores ≧3) while three (of eight) control animals consistently had lesion scores ≧3. In this challenge, all animals survived primary infection, and after its resolution, were evaluated over a five-week period for recurrent disease. The results are shown in FIG. 14B. The cumulative mean lesions scores for the V1Jns:ΔgB+V1Jns:gD-immunized group were clearly lower than those of the control group throughout the observation period; the overall reduction was significant (p<0.001). As was seen in the previous experiment, there were qualitative as well as quantitative differences in recurrences between the control and test groups. Unlike the control group, the V1Jns:ΔgB+V1Jns:gD group experienced an extended period free of recurrence beginning at observation day eight.

The results disclosed within this Example indicate that immunization of guinea pigs with DNA encoding HSV-2 gB sequences, or a mixture of DNAs encoding HSV-2 gD and gB sequences induces humoral immune responses to the encoded proteins, and those responses are associated with the reduction of primary and recurrent HSV-2-induced disease.

Additional studies in mice have shown that DNA immunization with V1Jns:ΔgB induces not only humoral but also cell-mediated immune responses.

Additional lymphoproliferative data in mice guinea pigs and monkeys (also, see Example 13 for primate data) indicate that immunization with V1Jns:ΔgB induces a memory response in all three models.

EXAMPLE 13

Young adult (2.2–7 kg body mass) seronegative male African green monkeys (3/group) were injected intramuscularly in one deltoid and one quadriceps with 0.5 ml of inoculum per site containing the indicated dosages of DNA. Control monkeys received a full human dose (15 μg of each HA antigen) of licensed influenza vaccine (Fluzone Whole Virion or Subvirion, Connaught Laboratories Inc., Swiftwater, Pa., USA; trivalent, 1992–93 formulation). Two immunizations were given as that is the recommended clinical protocol for immunization of humans without previous exposure to influenza virus.

Hemagglutination inhibiting (HI) antibodies were determined using 4 HA units of selected virus strain and chicken RBCs. Sera were incubated overnight with receptor-destroying enzyme (RDE, Sigma Chemical Co, St. Louis, Mo.), heated for 30 min at 56° C., and absorbed with chicken RBC.

Groups of six African green monkeys were immunized with DNA mixtures containing 100 or 10 μg each, of gD and gB DNA at 0 and 4 weeks, and were boosted at 24 weeks. Sera obtained at four-week intervals were analyzed for anti-gD and anti-gB antibodies with antigen-specific ELISAS. These ELISAs used cloned, baculovirus-expressed gD or truncated gB proteins as capture antigens and were originally qualified as antigen specific using sera from guinea pigs and mice immunized singly with V1jns:gD or V1jns:ΔgB (Example 11 and 12). Endpoint titers were taken as the reciprocal of the highest serum dilution giving an $OD_{405}$ signal ≧0.05 OD units above the signal obtained with the same dilution of preimmune serum from that animal. For purposes of calculation of geometric mean titers (GMT), sera negative at the lowest dilution tested were assigned an endpoint titer of 3. These sera were also surveyed for complement-dependent virus neutralization. Dilutions of heat inactivated serum were incubated with 200 plaque forming units (pfu) HSV-2 Curtis overnight at 4° C. Guinea pig complement was added for one hour at 37° C. before assaying for viable virus on Vero cells. The percent plaque reduction was determined (in duplicate) for each serum dilution compared to the same dilution of preimmune serum, scoring a 50% or greater reduction in plaque number as positive. Ten-fold serial dilutions ranging from 1:10 to 1:10,000 were assayed; endpoint titers were calculated by linear regression analysis. (Sera negative at the lowest dilution tested were assigned endpoint titers of 1.)

Figure 15A:
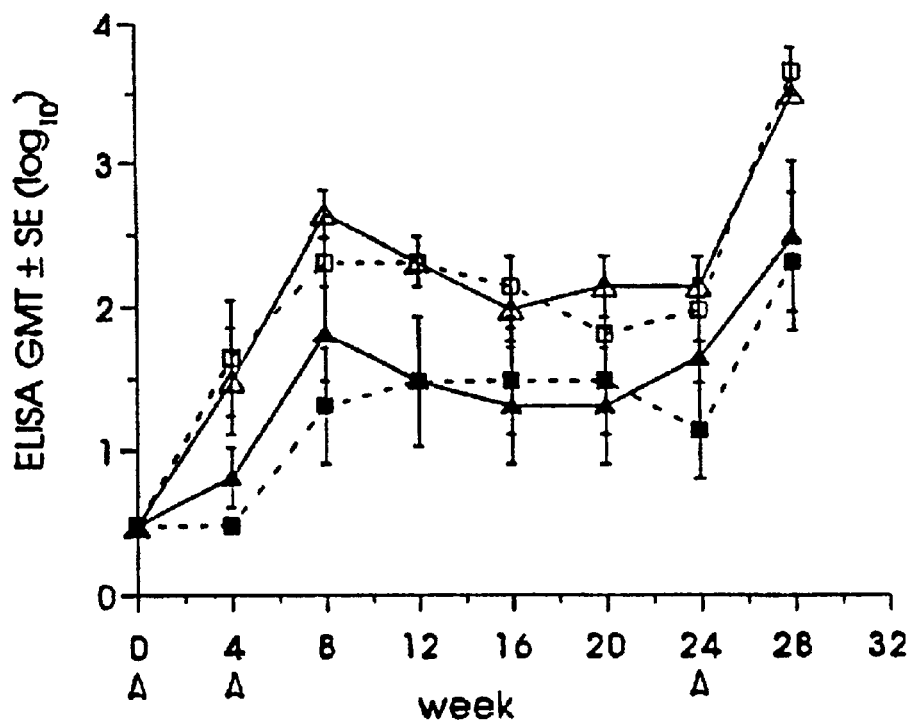
Figure 15B:
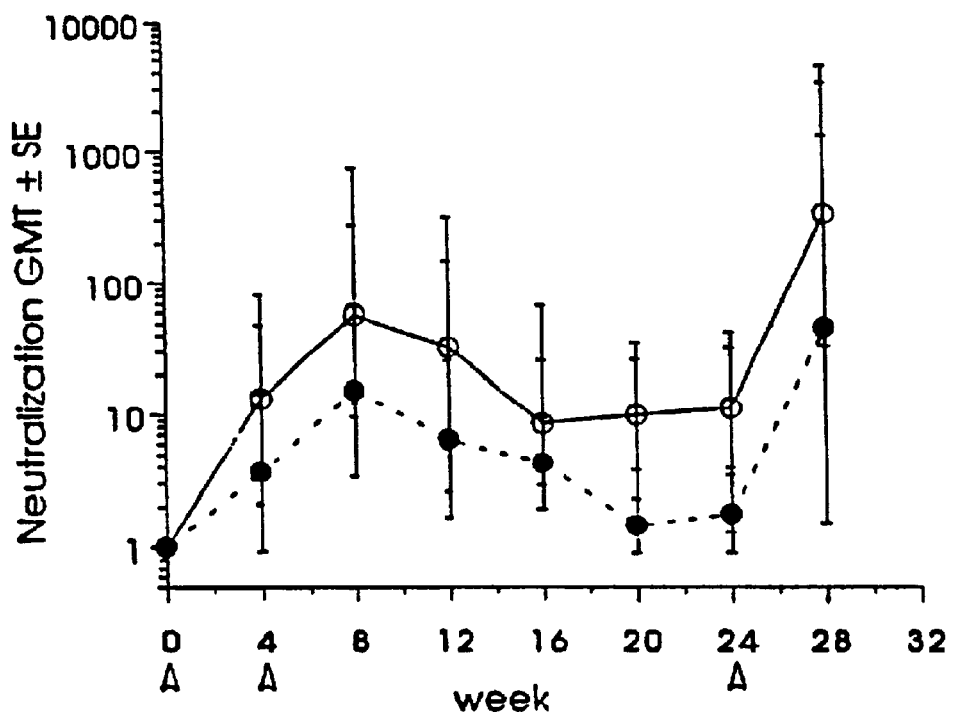

DNA from other pathogens also were found to induce humoral immune responses in African green monkeys. Immunization with DNAs encoding the herpes simplex virus (HSV) envelope glycoproteins D (gD DNA) and a truncated form of glycoprotein B (ΔgB DNA) induced antibody responses which were capable of neutralizing viral infectivity in vitro. After two immunizations with as little as 10 μg of each DNA construction, all animals had detectable neutralizing titers. As shown in FIG. 15A, the antibodies measured by an ELISA persisted out to 6 months following 2 immunizations and boosted with a subsequent injection. Neutralizing antibodies were generated, and although the titers declined, they were readily boostable as shown in FIG. 15B.

What is claimed is:

1. A plasmid expression vector which induces anti-HSV antibodies or protective immune responses upon introduction into vertebrate tissue, wherein said vector comprises at least one gene encoding a carboxy-terminal truncated gB protein comprising the amino terminal 707 amino acids of wild said gene or genes being operably linked to a transcription promoter.

2. The plasmid expression vector of claim 1 which is V1Jns:ΔgB.

3. A plasmid expression vector which induces anti-HSV antibodies or protective immune responses upon introduction into vertebrate tissue, wherein said vector comprises at least one gene encoding the HSV protein, gD, said gene or genes being operably linked to a transcription promoter.

4. The plasmid expression vector of claim 3 which is V1Jns:gD.

5. A vaccine for inducing an immune response against HSV which comprises a first plasmid expression vector which expresses the HSV protein gD and a second plasmid expression vector which expresses a carboxy-terminal truncated gB protein.

6. The plasmid expression vector of claim 5 wherein said gene encodes the HSV protein, gD.

7. A vaccine of claim 5 wherein said second plasmid expression vector is V1Jns:ΔgB.

8. A vaccine of claim 7 wherein said first plasmid expression vector is V1Jns:gD.

9. A method for inducing immune responses in a vertebrate against HSV epitopes which comprises introducing the vaccine according to claim 8 into a tissue of a vertebrate.

10. A vaccine of claim 8 further comprising a pharmaceutically acceptable carrier.

11. A method for inducing immune responses in a vertebrate against HSV epitopes which comprises introducing a plasmid expression vector into a tissue of a vertebrate, wherein said vector comprises at least one gene encoding at least one HSV protein or truncated protein, said gene or genes being operably linked to a transcription promoter.

12. A method for inducing immune responses in a vertebrate against HSV epitopes according to claim 11, wherein said vector comprises a gene which encodes an HSV protein selected from a group consisting of gB, gC, gD, gL, ICP27, and truncated gB.

13. A vaccine for inducing immune responses against HSV which comprises a plasmid expression vector comprising a gene encoding a carboxy-terminal truncated gB protein comprising the amino terminal 707 amino acides of wild type gB, said gene being operably linked to a transcription promoter, and a pharmaceutically acceptable carrier.

14. A vaccine of claim 13, wherein the plasmid expression vector is V1Jns:ΔgB.

15. A vaccine for inducing an immune response against HSV which comprises a plasmid expression vector comprising a gene which encodes the HSV protein, gD, said gene being operably linked to a transcription promoter, and a pharmaceutically acceptable carrier.

16. A vaccine of claim 15, wherein the plasmid xpression vector of is V1Jns:gD.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 23 base pairs
      (B) TYPE: nucleic acid

```
            (C) STRANDEDNESS: single
            (D) TOPOLOGY: linear (ii) MOLECULE TYPE: Other (ix) FEATURE:
            (A) NAME/KEY:
            (B) LOCATION: 1...23
            (D) OTHER INFORMATION: nucleic acid (xi) SEQUENCE DESCRIPTION: SEQ ID NO: 1:

CTATATAAGC AGAGCTCGTT TAG                                               23

(2) INFORMATION FOR SEQ ID NO: 2:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY:
            (B) LOCATION: 1...30
            (D) OTHER INFORMATION: nucleic acid (xi) SEQUENCE DESCRIPTION: SEQ ID NO: 2:

GTAGCAAAGA TCTAAGGACG GTGACTGCAG                                        30

(2) INFORMATION FOR SEQ ID NO: 3:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY:
            (B) LOCATION: 1...38
            (D) OTHER INFORMATION: nucleic acid (xi) SEQUENCE DESCRIPTION: SEQ ID NO: 3:

GTATGTGTCT GAAAATGAGC GTGGAGATTG GGCTCGCA                               38

(2) INFORMATION FOR SEQ ID NO: 4:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY:
            (B) LOCATION: 1...39
            (D) OTHER INFORMATION: nucleic acid (xi) SEQUENCE DESCRIPTION: SEQ ID NO: 4:

GTGCGAGCCC AATCTCCACG CTCATTTTCA GACACATAC                              39

(2) INFORMATION FOR SEQ ID NO: 5:

(i) SEQUENCE CHARACTERISTICS:
            (A) LENGTH: 78 base pairs
```

(B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...78
        (D) OTHER INFORMATION: nucleic acid (xi) SEQUENCE DESCRIPTION: SEQ ID NO: 5:

GATCACCATG GATGCAATGA AGAGAGGGCT CTGCTGTGTG CTGCTGCTGT GTGGAGCAGT    60

CTTCGTTTCG CCCAGCGA    78

(2) INFORMATION FOR SEQ ID NO: 6:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...78
        (D) OTHER INFORMATION: nucleic acid (xi) SEQUENCE DESCRIPTION: SEQ ID NO: 6:

GATCTCGCTG GGCGAAACGA AGACTGCTCC ACACAGCAGC AGCACACAGC AGAGCCCTCT    60

CTTCATTGCA TCCATGGT    78

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...27
        (D) OTHER INFORMATION: nucleic acid (xi) SEQUENCE DESCRIPTION: SEQ ID NO: 7:

GTACCTCATG AGCCACATAA TACCATG    27

(2) INFORMATION FOR SEQ ID NO: 8:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...40
        (D) OTHER INFORMATION: nucleic acid (xi) SEQUENCE DESCRIPTION: SEQ ID NO: 8:

GGTACAAGAT CTACCATGGC TTGCAATTGT CAGTTGATGC    40

(2) INFORMATION FOR SEQ ID NO: 9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...42
        (D) OTHER INFORMATION: nucleic acid (xi) SEQUENCE DESCRIPTION: SEQ ID NO: 9:

CCACATAGAT CTCCATGGGA ACTAAAGGAA GACGGTCTGT TC           42

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...33
        (D) OTHER INFORMATION: nucleic acid (xi) SEQUENCE DESCRIPTION: SEQ ID NO: 10:

GGTACAAATA TTGGCTATTG GCCATTGCAT ACG           33

(2) INFORMATION FOR SEQ ID NO: 11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...36
        (D) OTHER INFORMATION: nucleic acid (xi) SEQUENCE DESCRIPTION: SEQ ID NO: 11:

CCACATCTCG AGGAACCGGG TCAATTCTTC AGCACC           36

(2) INFORMATION FOR SEQ ID NO: 12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...38
        (D) OTHER INFORMATION: nucleic acid (xi) SEQUENCE DESCRIPTION: SEQ ID NO: 12:

GGTACAGATA TCGGAAAGCC ACGTTGTGTC TCAAAATC           38

-continued (2) INFORMATION FOR SEQ ID NO: 13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...37
        (D) OTHER INFORMATION: nucleic acid (xi) SEQUENCE DESCRIPTION: SEQ ID NO: 13:

CCACATGGAT CCGTAATGCT CTGCCAGTGT TACAACC        37

(2) INFORMATION FOR SEQ ID NO: 14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...39
        (D) OTHER INFORMATION: nucleic acid (xi) SEQUENCE DESCRIPTION: SEQ ID NO: 14:

GGTACATGAT CACGTAGAAA AGATCAAAGG ATCTTCTTG        39

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY:
        (B) LOCATION: 1...35
        (D) OTHER INFORMATION: nucleic acid (xi) SEQUENCE DESCRIPTION: SEQ ID NO: 15:

CCACATGTCG ACCCGTAAAA AGGCCGCGTT GCTGG        35